(12) United States Patent
Chinnaiyan et al.

(10) Patent No.: US 9,783,853 B2
(45) Date of Patent: Oct. 10, 2017

(54) RECURRENT GENE FUSIONS IN CANCER

(71) Applicant: THE REGENTS OF THE UNIVERSITY OF MICHIGAN, Ann Arbor, MI (US)

(72) Inventors: Arul Chinnaiyan, Plymouth, MI (US); Yi-Mi Wu, Ann Arbor, MI (US); Dan Robinson, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 221 days.

(21) Appl. No.: 14/329,639

(22) Filed: Jul. 11, 2014

(65) Prior Publication Data

US 2015/0017637 A1   Jan. 15, 2015

Related U.S. Application Data

(60) Provisional application No. 61/845,575, filed on Jul. 12, 2013.

(51) Int. Cl.
*C12Q 1/68* (2006.01)
*G01N 33/574* (2006.01)

(52) U.S. Cl.
CPC ..... *C12Q 1/6886* (2013.01); *G01N 33/57492* (2013.01); *C12Q 2600/156* (2013.01); *G01N 2333/71* (2013.01)

(58) Field of Classification Search
None
See application file for complete search history.

(56) References Cited

U.S. PATENT DOCUMENTS

2012/0142549 A1   6/2012   Chinnaiyan et al.
2013/0096012 A1   4/2013   Qian et al.

FOREIGN PATENT DOCUMENTS

WO    2013089882 A2    6/2013

OTHER PUBLICATIONS

Wu et al. (Cancer Discovery, 2013, 3:636-647, first published online Apr. 4, 2013.*
Maher et al. (Nature, 2009, vol. 458, pp. 97-103).*
Bastarrachea et al., "Obesity as an adverse prognostic factor for patients receiving adjuvant chemotherapy for breast cancer." Ann Intern Med. Jan. 1, 1994;120(1):18-25.
Brooks et al., "Molecular pathways: fibroblast growth factor signaling: a new therapeutic opportunity in cancer." Clinical Cancer Research 18.7 (2012): 1855-1862.
Browman et al., "The SPFH domain-containing proteins: more than lipid raft markers." Trends Cell Biol. Aug. 2007; 17(8):394-402.
Chai et al., "Crystal structure of a procaspase-7 zymogen: mechanisms of activation and substrate binding." Cell. Nov. 2, 2001; 107(3):399-407.
Edwards et al., "Infiltrating ductal carcinoma of the breast: the survival impact of race." J Clin Oncol. Aug. 1998; 16(8):2693-9.
Elledge et al., "Tumor biologic factors and breast cancer prognosis among white, Hispanic, and black women in the United States." J Natl Cancer Inst. May 4, 1994; 86(9):705-12.
Greulich & Pollock, "Targeting mutant fibroblast growth factor receptors in cancer." Trends Mol Med. May 2011; 17(5):283-92.
Guagnano et al., "FGFR genetic alterations predict for sensitivity to NVP-BGJ398, a selective pan-FGFR inhibitor." Cancer Discov. Dec. 2012; 2(12):1118-33.
Ishizaki et al., "p160ROCK a Rho-associated coiled-coil forming protein kinase, works downstream of Rho and induces focal adhesions." FEBS Lett. Mar. 10, 1997; 404(2-3):118-24.
Jackson et al., "8p11 myeloproliferative syndrome: a review." Hum Pathol. Apr. 2010; 41(4):461-76.
Knight et al., "A human sterile alpha motif domain polymerizome." Protein Sci. Oct. 2011; 20(10):1697-706.
Mateja et al., "The dimerization mechanism of LIS1 and its implication for proteins containing the LisH motif." J Mol Biol. Mar. 24, 2006;357(2):621-31.
Miyake et al., "1-tert-butyl-3-[6-(3,5-dimethoxy-phenyl)-2-(4-diethylamino-butylamino)-pyrido[2,3-d]pyrimidin-7-yl]-urea (PD173074), a selective tyrosine kinase inhibitor of fibroblast growth factor receptor-3 (FGFR3), inhibits cell proliferation of bladder cancer carrying the FGFR3 gene mutation along with up-regulation of p27/Kip1 and G1/G0 arrest." J Pharmacol Exp Ther. Mar. 2010; 332(3):795-802.
Peter et al., "BAR domains as sensors of membrane curvature: the amphiphysin BAR structure." Science. Jan. 23, 2004; 303(5657):495-9.
Singh et al., "Transforming fusions of FGFR and TACC genes in human glioblastoma." Science. Sep. 7, 2012; 337(6099):1231-5.
Tomlins et al., "Distinct classes of chromosomal rearrangements create oncogenic ETS gene fusions in prostate cancer." Nature. Aug. 2, 2007; 448(7153):595-9.
Tong et al., "Characterization of the promoter region and oligomerization domain of H4 (D10S170), a gene frequently rearranged with the ret proto-oncogene." Oncogene. May 4, 1995; 10(9):1781-7.
Turner & Grose, "Fibroblast growth factor signalling: from development to cancer." Nat Rev Cancer. Feb. 2010;10(2):116-29.
Wesche et al., "Fibroblast growth factors and their receptors in cancer." Biochem J. Jul. 15, 2011; 437(2):199-213.
Yagasaki et al., "Fusion of ETV6 to fibroblast growth factor receptor 3 in peripheral T-cell lymphoma with a t(4;12)(p16;p13) chromosomal translocation." Cancer Res. Dec. 1, 2001; 61(23):8371-4.
Wu et al., "Identification of targetable FGFR gene fusions in diverse cancers." Cancer Discov. Jun. 2013; 3(6):636-47.
Arai et al., "Fibroblast growth factor receptor 2 tyrosine kinase fusions define a unique molecular subtype of cholangiocarcinoma." Hepatology. Apr. 2014;59(4):1427-34.
Search report of related European application No. 14822575.8, mailed Jan. 11, 2017, 8 pages.

* cited by examiner

*Primary Examiner* — Juliet Switzer

(74) *Attorney, Agent, or Firm* — Casimir Jones, S.C.

(57) ABSTRACT

The present disclosure relates to compositions and methods for cancer diagnosis, research and therapy, including but not limited to, cancer markers. In particular, the present disclosure relates to gene fusions as diagnostic markers and clinical targets for cancer.

6 Claims, 16 Drawing Sheets

FGFR2 fusions

FGFR3 fusions

FGFR1 fusions

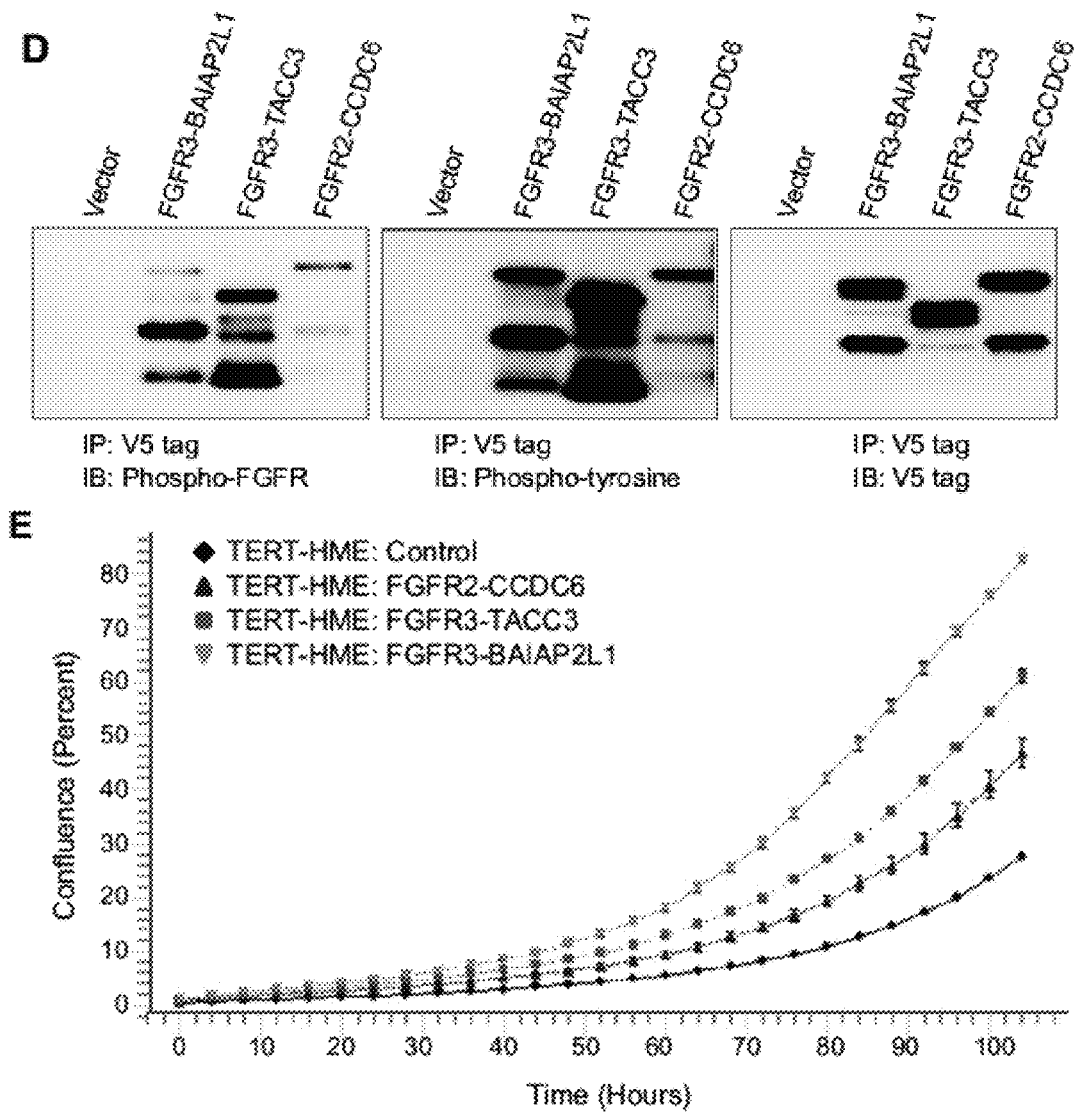

```
                            SEQUENCE LISTING

<160> NUMBER OF SEQ ID NOS: 37

<210> SEQ ID NO 1
<211> LENGTH: 42
<212> TYPE: DNA
<213> ORGANISM: artificial sequence
<220> FEATURE:
<223> OTHER INFORMATION: Synthetic

<400> SEQUENCE: 1
agaccagaat tgcaaggcca ggtccgttat gccacctgga gc                            42

<210> SEQ ID NO 2
<211> LENGTH: 42
<212> TYPE: DNA
<213> ORGANISM: artificial sequence
<220> FEATURE:
<223> OTHER INFORMATION: Synthetic

<400> SEQUENCE: 2
ccgcagaaac tacgagttga tggtcagttt gaaaaggagg at                            42

<210> SEQ ID NO 3
<211> LENGTH: 42
<212> TYPE: DNA
<213> ORGANISM: artificial sequence
<220> FEATURE:
<223> OTHER INFORMATION: Synthetic

<400> SEQUENCE: 3
ctcactctca caaccaatga ggagagtaga tctggagaaa cc                            42

<210> SEQ ID NO 4
<211> LENGTH: 42
<212> TYPE: DNA
<213> ORGANISM: artificial sequence
<220> FEATURE:
<223> OTHER INFORMATION: Synthetic

<400> SEQUENCE: 4
ctcactctca caaccaatga gatcatggag gaaacaaata cg                            42

<210> SEQ ID NO 5
<211> LENGTH: 42
<212> TYPE: DNA
<213> ORGANISM: artificial sequence
<220> FEATURE:
<223> OTHER INFORMATION: Synthetic

<400> SEQUENCE: 5
ctcactctca caaccaatga gatggcagat gatcagggct gt                            42

<210> SEQ ID NO 6
<211> LENGTH: 42
<212> TYPE: DNA
<213> ORGANISM: artificial sequence
<220> FEATURE:
<223> OTHER INFORMATION: Synthetic

<400> SEQUENCE: 6
ctcactctca caaccaatga gcaagccagg gctgagcagg aa                            42
```

<210> SEQ ID NO 7
<211> LENGTH: 42
<212> TYPE: DNA
<213> ORGANISM: artificial sequence
<220> FEATURE:
<223> OTHER INFORMATION: Synthetic

<400> SEQUENCE: 7
ctcactctca caaccaatga gggtggggag aaacagcggg tc                42

<210> SEQ ID NO 8
<211> LENGTH: 42
<212> TYPE: DNA
<213> ORGANISM: artificial sequence
<220> FEATURE:
<223> OTHER INFORMATION: Synthetic

<400> SEQUENCE: 8
ctcactctca caaccaatga gacacaactt cgaaaccagc ta                42

<210> SEQ ID NO 9
<211> LENGTH: 42
<212> TYPE: DNA
<213> ORGANISM: artificial sequence
<220> FEATURE:
<223> OTHER INFORMATION: Synthetic

<400> SEQUENCE: 9
acagccgcgc gcctcggcca gtgactgcag cagcagcggc ag                42

<210> SEQ ID NO 10
<211> LENGTH: 42
<212> TYPE: DNA
<213> ORGANISM: artificial sequence
<220> FEATURE:
<223> OTHER INFORMATION: Synthetic

<400> SEQUENCE: 10
cttaccgtga cgtccaccga caatgttatg gaacagttca at                42

<210> SEQ ID NO 11
<211> LENGTH: 42
<212> TYPE: DNA
<213> ORGANISM: artificial sequence
<220> FEATURE:
<223> OTHER INFORMATION: Synthetic

<400> SEQUENCE: 11
cttaccgtga cgtccaccga cgtgccaggc ccaccccag gt                42

<210> SEQ ID NO 12
<211> LENGTH: 42
<212> TYPE: DNA
<213> ORGANISM: artificial sequence
<220> FEATURE:
<223> OTHER INFORMATION: Synthetic

<400> SEQUENCE: 12
cttaccgtga cgtccaccga cgtaaaggcg acacaggagg ag                42

<210> SEQ ID NO 13
<211> LENGTH: 42
<212> TYPE: DNA
<213> ORGANISM: artificial sequence
<220> FEATURE:

<223> OTHER INFORMATION: Synthetic

<400> SEQUENCE: 13
gctgaggtgt ggggcgggcc ttctggccca ggtgccctgg ct        42

<210> SEQ ID NO 14
<211> LENGTH: 37
<212> TYPE: DNA
<213> ORGANISM: artificial sequence
<220> FEATURE:
<223> OTHER INFORMATION: Synthetic

<400> SEQUENCE: 14
caacggtccg accatggtca gctggggtcg tttcatc              37

<210> SEQ ID NO 15
<211> LENGTH: 30
<212> TYPE: DNA
<213> ORGANISM: artificial sequence
<220> FEATURE:
<223> OTHER INFORMATION: Synthetic

<400> SEQUENCE: 15
gaacggaccg aaaggctggg aggaggggtg                      30

<210> SEQ ID NO 16
<211> LENGTH: 32
<212> TYPE: DNA
<213> ORGANISM: artificial sequence
<220> FEATURE:
<223> OTHER INFORMATION: Synthetic

<400> SEQUENCE: 16
gaacggaccg cggccactga cactagcaat gt                   32

<210> SEQ ID NO 17
<211> LENGTH: 29
<212> TYPE: DNA
<213> ORGANISM: artificial sequence
<220> FEATURE:
<223> OTHER INFORMATION: Synthetic

<400> SEQUENCE: 17
caacggtccg accatgggcg ccctgcct                        29

<210> SEQ ID NO 18
<211> LENGTH: 33
<212> TYPE: DNA
<213> ORGANISM: artificial sequence
<220> FEATURE:
<223> OTHER INFORMATION: Synthetic

<400> SEQUENCE: 18
caacggaccg atcttctcca tcttggagat gag                  33

<210> SEQ ID NO 19
<211> LENGTH: 33
<212> TYPE: DNA
<213> ORGANISM: artificial sequence
<220> FEATURE:
<223> OTHER INFORMATION: Synthetic

<400> SEQUENCE: 19
caacggaccg atcttctcca tcttggagat gag                  33

```
<210> SEQ ID NO 20
<211> LENGTH: 39
<212> TYPE: DNA
<213> ORGANISM: artificial sequence
<220> FEATURE:
<223> OTHER INFORMATION: Synthetic

<400> SEQUENCE: 20
caacggtccg accatgaatg ttatggaaca gttcaatcc                                39

<210> SEQ ID NO 21
<211> LENGTH: 32
<212> TYPE: DNA
<213> ORGANISM: artificial sequence
<220> FEATURE:
<223> OTHER INFORMATION: Synthetic

<400> SEQUENCE: 21
gaacggaccg cgaatgatgg gtgccgagcg at                                       32

<210> SEQ ID NO 22
<211> LENGTH: 41
<212> TYPE: DNA
<213> ORGANISM: artificial sequence
<220> FEATURE:
<223> OTHER INFORMATION: Synthetic

<400> SEQUENCE: 22
gaacggtccg accatgatca tggaggaaac aaatacgcag a                             41

<210> SEQ ID NO 23
<211> LENGTH: 33
<212> TYPE: DNA
<213> ORGANISM: artificial sequence
<220> FEATURE:
<223> OTHER INFORMATION: Synthetic

<400> SEQUENCE: 23
caacggaccg ccactgacac tagcaatgtc tga                                      33

<210> SEQ ID NO 24
<211> LENGTH: 40
<212> TYPE: DNA
<213> ORGANISM: artificial sequence
<220> FEATURE:
<223> OTHER INFORMATION: Synthetic

<400> SEQUENCE: 24
caacggtccg accatggtgc caggcccacc cccaggtgtt                               40

<210> SEQ ID NO 25
<211> LENGTH: 33
<212> TYPE: DNA
<213> ORGANISM: artificial sequence
<220> FEATURE:
<223> OTHER INFORMATION: Synthetic

<400> SEQUENCE: 25
caacggaccg atcttctcca tcttggagat gag                                      33

<210> SEQ ID NO 26
<211> LENGTH: 41
<212> TYPE: DNA
<213> ORGANISM: artificial sequence
<220> FEATURE:
<223> OTHER INFORMATION: Synthetic
```

<400> SEQUENCE: 26
gaacggtccg accatgggtg gggagaaaca gcgggtcttc a            41

<210> SEQ ID NO 27
<211> LENGTH: 33
<212> TYPE: DNA
<213> ORGANISM: artificial sequence
<220> FEATURE:
<223> OTHER INFORMATION: Synthetic

<400> SEQUENCE: 27
cttcggaccg ttgctaggtg ccggctcctc ctt                     33

<210> SEQ ID NO 28
<211> LENGTH: 40
<212> TYPE: DNA
<213> ORGANISM: artificial sequence
<220> FEATURE:
<223> OTHER INFORMATION: Synthetic

<400> SEQUENCE: 28
gaacggtccg accatgcaag ccagggctga gcaggaagaa              40

<210> SEQ ID NO 29
<211> LENGTH: 30
<212> TYPE: DNA
<213> ORGANISM: artificial sequence
<220> FEATURE:
<223> OTHER INFORMATION: Synthetic

<400> SEQUENCE: 29
gaacggaccg aaaggctggg aggaggggtg                         30

<210> SEQ ID NO 30
<211> LENGTH: 42
<212> TYPE: DNA
<213> ORGANISM: artificial sequence
<220> FEATURE:
<223> OTHER INFORMATION: Synthetic

<400> SEQUENCE: 30
caacggtccg accatggcac atagagatga atccagcgc aa            42

<210> SEQ ID NO 31
<211> LENGTH: 33
<212> TYPE: DNA
<213> ORGANISM: artificial sequence
<220> FEATURE:
<223> OTHER INFORMATION: Synthetic

<400> SEQUENCE: 31
caacggaccg actgaagact ggtcccagac ctt                     33

<210> SEQ ID NO 32
<211> LENGTH: 20
<212> TYPE: DNA
<213> ORGANISM: artificial sequence
<220> FEATURE:
<223> OTHER INFORMATION: Synthetic

<400> SEQUENCE: 32
ccaactgcac caacgaactg                                    20

<210> SEQ ID NO 33
<211> LENGTH: 20

```
<212> TYPE: DNA
<213> ORGANISM: artificial sequence
<220> FEATURE:
<223> OTHER INFORMATION: Synthetic

<400> SEQUENCE: 33
gtggaagcca ggtcatctcc                                                      20

<210> SEQ ID NO 34
<211> LENGTH: 20
<212> TYPE: DNA
<213> ORGANISM: artificial sequence
<220> FEATURE:
<223> OTHER INFORMATION: Synthetic

<400> SEQUENCE: 34
gctgctgaag gaaggacaca                                                      20

<210> SEQ ID NO 35
<211> LENGTH: 20
<212> TYPE: DNA
<213> ORGANISM: artificial sequence
<220> FEATURE:
<223> OTHER INFORMATION: Synthetic

<400> SEQUENCE: 35
atggccaagc aatctgcgta                                                      20

<210> SEQ ID NO 36
<211> LENGTH: 20
<212> TYPE: DNA
<213> ORGANISM: artificial sequence
<220> FEATURE:
<223> OTHER INFORMATION: Synthetic

<400> SEQUENCE: 36
gacctggacc gtgtccttac                                                      20

<210> SEQ ID NO 37
<211> LENGTH: 20
<212> TYPE: DNA
<213> ORGANISM: artificial sequence
<220> FEATURE:
<223> OTHER INFORMATION: Synthetic

<400> SEQUENCE: 37
gatcttggcc actccatcgt                                                      20
```

RECURRENT GENE FUSIONS IN CANCER

The present application claims priority to U.S. Provisional Patent Application Ser. No. 61/845,575, filed Jul. 12, 2013, the disclosure of which is herein incorporated by reference in its entirety.

GOVERNMENT SUPPORT

This invention was made with government support under CA111275, CA132874, and CA069568 awarded by the National Institutes of Health and W81XWH-08-1-0110 awarded by the Army/MRMC. The government has certain rights in the invention.

FIELD OF THE INVENTION

The present disclosure relates to compositions and methods for cancer diagnosis, research and therapy, including but not limited to, cancer markers. In particular, the present disclosure relates to gene fusions as diagnostic markers and clinical targets for cancer.

BACKGROUND OF THE INVENTION

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of ER and PR levels.

Prognosis and selection of therapy are influenced by the age of the patient, stage of the disease, pathologic characteristics of the primary tumor including the presence of tumor necrosis, estrogen-receptor (ER) and progesterone-receptor (PR) levels in the tumor tissue, HER2 overexpression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor downregulators), and monoclonal antibody treatment (e.g., against HER2). They may be used separately or, most often, in different combinations.

There is a need for additional diagnostic and treatment options, particularly treatments customized to a patient's tumor.

SUMMARY OF THE INVENTION

The present disclosure relates to compositions and methods for cancer diagnosis, research and therapy, including but not limited to, cancer markers. In particular, the present disclosure relates to gene fusions as diagnostic markers and clinical targets for cancer.

In some embodiments, the present invention provides a kit for detecting gene fusions associated with cancer a subject, comprising, consisting essentially of, or consisting of: at least a first gene fusion informative reagent for identification of a gene fusion selected from, for example, SLC45A3-FGFR2; FGFR2-KIAA1967; FGFR2-OFD1; and FGF1-Bag4. In some embodiments, the reagent is, for example, a probe that specifically hybridizes to the fusion junction of the gene fusion, a pair of primers that amplify a fusion junction of the gene fusion (e.g., a first primer that hybridizes to a 5' member of the gene fusion and second primer that hybridizes to a 3' member of the gene fusion), an antibody that binds to the fusion junction of the gene fusion polypeptide, a sequencing primer that binds to the gene fusion and generates an extension product that spans the fusion junction of the gene fusion, or a pair of probes wherein the first probe hybridizes to a 5' member of the gene fusion and the second probe hybridizes to a 3' member of the gene fusion gene. In some embodiments, the reagent is labeled. In some embodiments, the cancer is breast cancer, bladder cancer, prostate cancer, or cholangiocarcinoma.

Further embodiments of the present invention provide a method for identifying cancer in a patient comprising: (a) contacting a biological sample from a subject with a nucleic acid or polypeptide detection assay comprising: at least a first gene fusion informative reagent for identification of a gene fusion selected from, for example, SLC45A3-FGFR2; FGFR2-KIAA1967; FGFR2-OFD1; and FGF1-Bag4; and (b) identifying cancer in the subject when the gene fusion is present in the sample. In some embodiments, the sample is, for example, tissue, blood, plasma, serum, cells or tissues. In some embodiments, the cancer is, for example, breast cancer, bladder cancer, prostate cancer, or cholangiocarcinoma. In some embodiments, the method further comprises the step of determining a treatment course of action based on the presence or absence of the gene fusion in the sample. In some embodiments, the treatment course of action comprises administration of a gene fusion pathway inhibitor when the gene fusion is present in the sample.

Additional embodiments of the present disclosure are provided in the description and examples below.

DEFINITIONS

Figure 1:
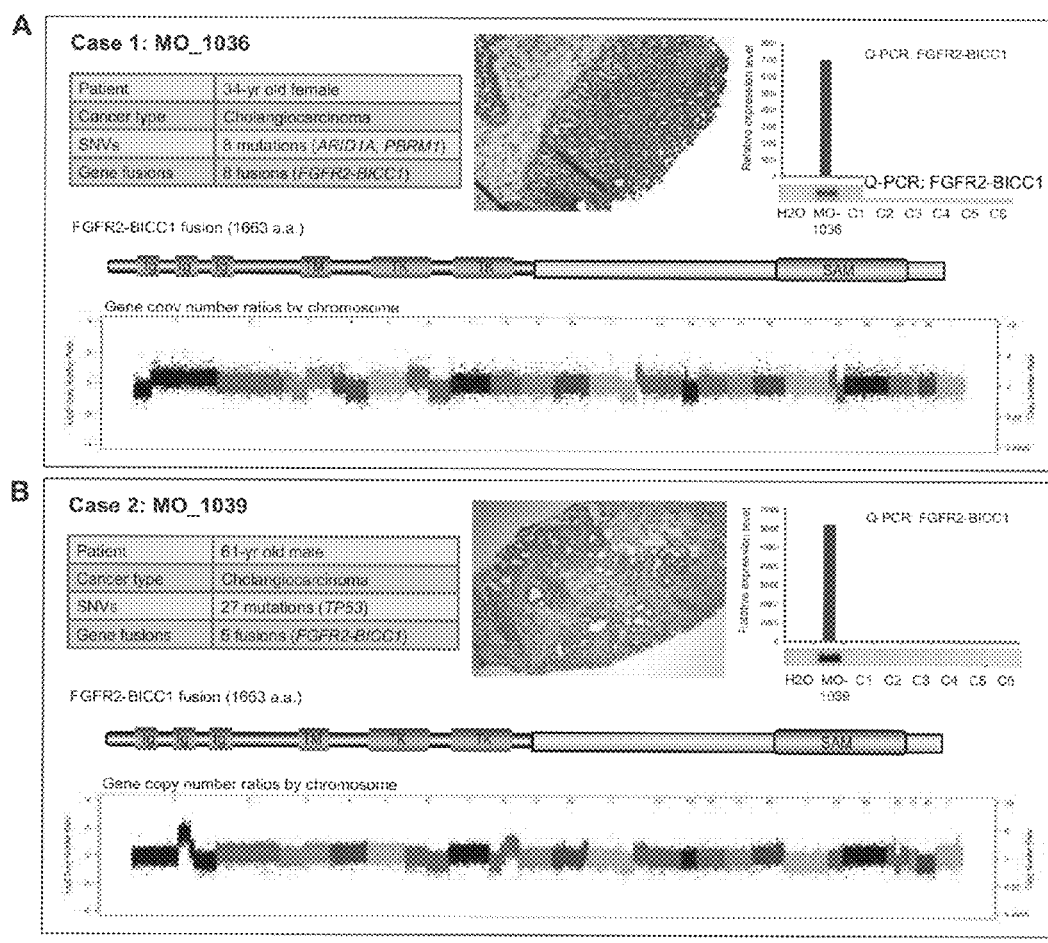
FIG. 1 shows integrative sequencing and mutational analysis of four index cancer patients found to harbor FGFR fusions. The four index cases shown are (a) cholangiocarcinoma, (b) cholangiocarcinoma, (c) breast cancer, and (d) prostate cancer.
Figure 1:
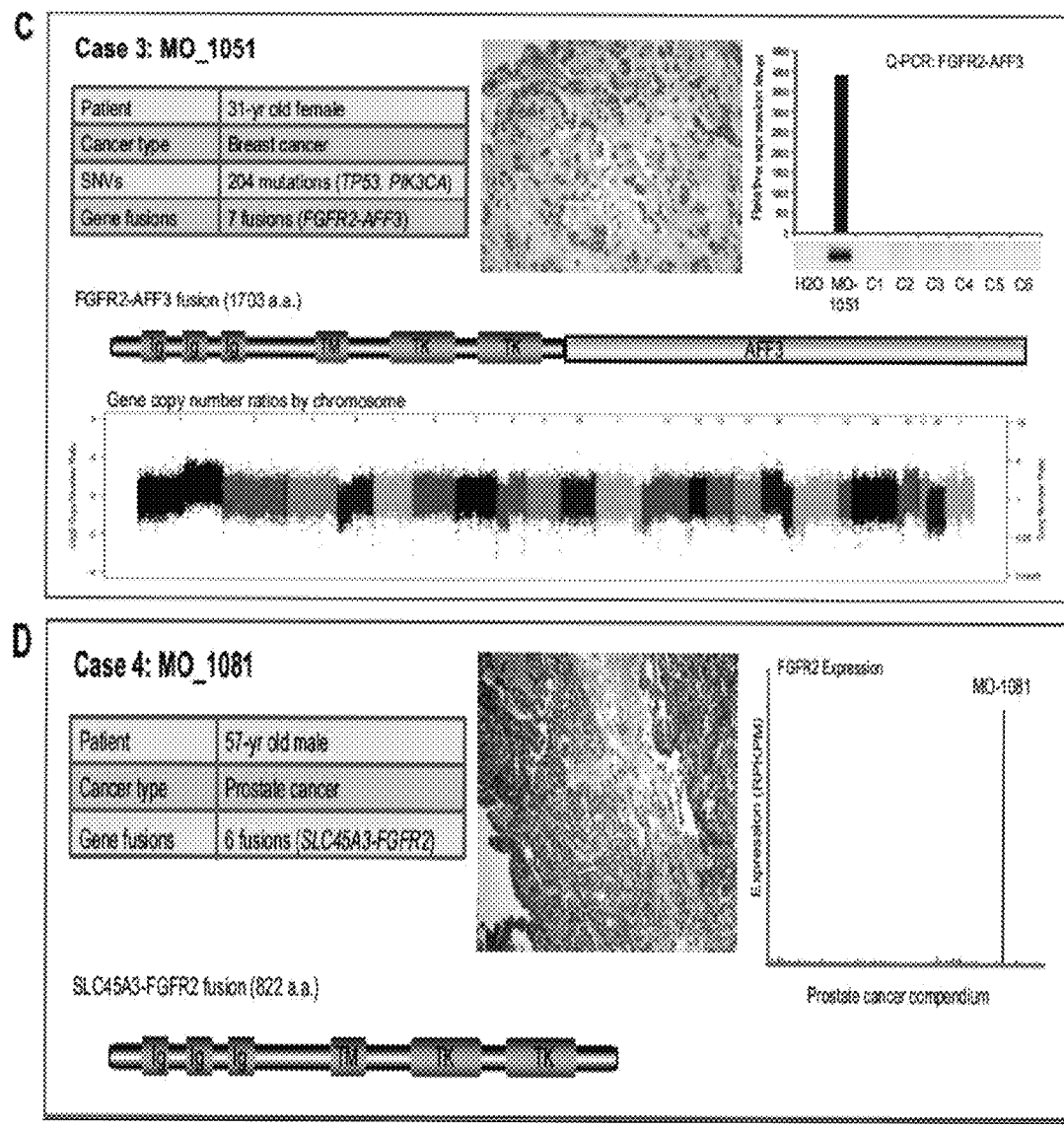

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

As used herein, the term "gene fusion" refers to a chimeric genomic DNA, a chimeric messenger RNA, a truncated protein or a chimeric protein resulting from the fusion of at least a portion of a first gene to at least a portion of a second gene. In some embodiments, gene fusions involve internal deletions of genomic DNA within a single gene (e.g., no second gene is involved in the fusion). The gene fusion need not include entire genes or exons of genes.

As used herein, the term "gene upregulated in cancer" refers to a gene that is expressed (e.g., mRNA or protein expression) at a higher level in cancer (e.g., breast cancer) relative to the level in other tissue. In this context, "other tissue" may refer to, for example, tissues from different organs in the same subject or to normal tissues of the same or different type. In some embodiments, genes upregulated in cancer are expressed at a level between at least 10% to 300% higher than the level of expression in other tissue. For example, genes upregulated in cancer are frequently expressed at a level preferably at least 25%, at least 50%, at least 100%, at least 200%, or at least 300% higher than the level of expression in other tissue.

As used herein, the term "gene upregulated in breast tissue" refers to a gene that is expressed (e.g., mRNA or protein expression) at a higher level in breast tissue relative to the level in other tissue. In some embodiments, genes upregulated in breast tissue are expressed at a level between at least 10% to 300%. For example, genes upregulated in cancer are frequently expressed at a level preferably at least 25%, at least 50%, at least 100%, at least 200%, or at least 300% higher than the level of expression in other tissues. In some embodiments, genes upregulated in breast tissue are exclusively expressed in breast tissue.

As used herein, the term "transcriptional regulatory region" refers to the region of a gene comprising sequences that modulate (e.g., upregulate or downregulate) expression of the gene. In some embodiments, the transcriptional regulatory region of a gene comprises a non-coding upstream sequence of a gene, also called the 5' untranslated region (5'UTR). In other embodiments, the transcriptional regulatory region contains sequences located within the coding region of a gene or within an intron (e.g., enhancers).

As used herein, the terms "detect", "detecting" or "detection" may describe either the general act of discovering or discerning or the specific observation of a detectably labeled composition.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "probe" refers to an oligonucleotide, whether occurring naturally as in a purified restriction digest or produced synthetically, recombinantly or by PCR amplification, which is capable of hybridizing to at least a portion of another oligonucleotide of interest. A probe may be single-stranded or double-stranded. Probes are useful in the detection, identification and isolation of particular gene sequences. It is contemplated that any probe used in methods of the present disclosure will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the methods or reagents of the present disclosure be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. An isolated nucleic acid is present in a form or setting that is different from that in which it is found in nature. In contrast, non-isolated nucleic acids are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the nucleic acid, oligonucleotide or polynucleotide often will contain, at a minimum, the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids (e.g., biological fluids such as blood, serum, urine, etc), solids, tissues (e.g., biopsy tissue), cells, biological macromolecules (e.g., nucleic acids and polypeptides), and gases. Biological samples include blood products, such as plasma, serum and the like. Such examples are not however to be construed as limiting the sample types applicable to the present invention.

DETAILED DESCRIPTION OF THE INVENTION

Provided herein are compositions and methods for cancer diagnosis, research and therapy, including but not limited to, cancer markers. In particular, the present disclosure relates to gene fusions as diagnostic markers and clinical targets for cancer.

I. Gene Fusions

The present disclosure identifies recurrent gene fusions indicative of cancer (e.g., breast cancer). In some embodiments, the gene fusions are the result of a chromosomal rearrangement of a first and second gene resulting in a gene fusion. Example gene fusions include, but are not limited to SLC45A3-FGFR2; FGFR2-KIAA1967; FGFR2-OFD1; and FGF1-Bag4.

Solute carrier family 45, member 3 (SLC45A3) has the GenBank accession number NM_033102. fibroblast growth factor receptor 2 (FGFR2) has the GenBank accession number AF097336. KIAA1967 has the GenBank accession number BC065495. Oral-facial-digital syndrome 1 (OFD1) has the GenBank accession number NM_003611. BCL2-associated athanogene 4 (BAG4) has the GenBank accession number NM_004874.

II. Antibodies

The gene fusion proteins of the present disclosure, including fragments, derivatives and analogs thereof, may be used as immunogens to produce antibodies having use in the diagnostic, screening, research, and therapeutic methods described below. The antibodies may be polyclonal or monoclonal, chimeric, humanized, single chain, Fv or Fab fragments. Various procedures known to those of ordinary skill in the art may be used for the production and labeling of such antibodies and fragments. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). Antibodies or fragments exploiting the differences between the truncated or chimeric protein resulting from a gene fusion and their respective native proteins are particularly preferred (e.g., the antibody preferentially binds to the protein expressed by the gene fusion relative to its binding to the protein generated by the non-fusion gene(s)).

III. Diagnostic and Screening Applications

The gene fusions described herein may be detectable as DNA, RNA or protein. Initially, the gene fusion is detectable as a chromosomal rearrangement of genomic DNA having a 5' portion from a first gene and a 3' portion from a second. Once transcribed, the gene fusion may be detectable as a chimeric mRNA having a 5' portion from a first gene and a 3' portion from a second gene or a chimeric mRNA with a deletion of mRNA. Once translated, the gene fusion may be detectable as fusion of a 5' portion from a first protein and a 3' portion from a second protein or a truncated version of a first or second protein. The truncated or fusion proteins may differ from their respective native proteins in amino acid sequence, post-translational processing and/or secondary, tertiary or quaternary structure. Such differences are used to identify the presence of the gene fusion. Specific methods of detection are described in more detail below.

The present disclosure provides DNA, RNA and protein based diagnostic, prognostic and screening methods that either directly or indirectly detect the gene fusions. The present disclosure also provides compositions and kits for diagnostic and screening purposes.

The diagnostic and screening methods of the present disclosure may be qualitative or quantitative. Quantitative methods may be used, for example, to discriminate between indolent and aggressive cancers via a cutoff or threshold level. Where applicable, qualitative or quantitative methods of embodiments of the disclosure include amplification of a target, a signal or an intermediary.

An initial assay may confirm the presence of a gene fusion but not identify the specific fusion. A secondary assay may then be performed to determine the identity of the particular fusion, if desired. The second assay may use a different detection technology than the initial assay.

The gene fusions may be detected along with other markers in a multiplex or panel format. Markers are selected for their predictive value alone or in combination with the gene fusions. Exemplary breast cancer markers include, but are not limited to those described in U.S. Pat. Nos. 5,622,829, 5,720,937, 6,294,349, each of which is herein incorporated by reference in its entirety. Markers for other cancers, diseases, infections, and metabolic conditions are also contemplated for inclusion in a multiplex or panel format.

The diagnostic methods may also be modified with reference to data correlating particular gene fusions with the stage, aggressiveness or progression of the disease or the presence or risk of metastasis. Ultimately, the information provided assists a physician in choosing the best course of treatment for a particular patient.

A. Sample

Any sample suspected of containing the gene fusions may be tested according to the methods of the present disclosure. By way of non-limiting example, the sample may be tissue (e.g., a breast, prostate, bladder or epithelial biopsy sample or a tissue sample obtained by surgery), blood, cell secretions, urine, semen, prostate secretions, or a fraction thereof (e.g., plasma, serum, exosomes, etc.).

The patient sample typically involves preliminary processing designed to isolate or enrich the sample for the gene fusion(s) or cells that contain the gene fusion(s). A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

B. DNA and RNA Detection

The gene fusions of the present disclosure may be detected as chromosomal rearrangements of genomic DNA or chimeric mRNA using a variety of nucleic acid techniques known to those of ordinary skill in the art, including but not limited to: nucleic acid sequencing; nucleic acid hybridization; and, nucleic acid amplification.

1. Sequencing

In some embodiments, nucleic acid sequencing methods are utilized for detection. In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbial., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbial., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbial., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. Nos. 11/671,956; 11/781,166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

In some embodiments, detection methods utilize hybridization assays. Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with radio-, fluorescent- or antigen-labeled bases is localized and quantitated in the tissue using autoradiography, fluorescence microscopy or immunohistochemistry. ISH can also use two or more probes, labeled with radioactivity or the other non-radioactive labels, to simultaneously detect two or more transcripts.

a. FISH

In some embodiments, fusion sequences are detected using fluorescence in situ hybridization (FISH). The preferred FISH assays for methods of embodiments of the present disclosure utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

b. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

Southern and Northern blotting may be used to detect specific DNA or RNA sequences, respectively. In these techniques DNA or RNA is extracted from a sample, fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g. U.S. Pat. Nos. 5,399,491 and 5,824,518, each of which is herein incorporated by reference in its entirety. In a variation described in U.S. Pat. No. 7,374,885 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase;

a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified gene fusion nucleic acids can be detected by any conventional means. For example, the gene fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs, including fluorescence resonance energy transfer (FRET) labels, are disclosed in, for example U.S. Pat. Nos. 6,534,274 and 5,776,782, each of which is herein incorporated by reference in its entirety.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through standard fluorometric detection means well known in the art (e.g., using a fluorimeter).

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. See, e.g. U.S. Pat. No. 5,814,447 (herein incorporated by reference in its entirety).

C. Protein Detection

The gene fusions of the present disclosure may be detected as truncated or chimeric proteins using a variety of protein techniques known to those of ordinary skill in the art, including but not limited to: protein sequencing and immunoassays.

1. Sequencing

Illustrative non-limiting examples of protein sequencing techniques include, but are not limited to, mass spectrometry and Edman degradation.

Mass spectrometry can, in principle, sequence any size protein. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction (see, e.g., Edman, Acta Chem. Scand. 4:283-93 (1950)), the peptide to be sequenced is adsorbed onto a solid surface (e.g., a glass fiber coated with polybrene). Though there are various well known modifications to this procedure (including automated modifications), one exemplary method involves the use of the Edman reagent, phenylisothiocyanate (PITC), which is added, together with a mildly basic buffer solution of 12% trimethylamine, to an adsorbed peptide, and which reacts with the amine group of the N-terminal amino acid of the adsorbed peptide. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about or over 98%, which allows about 50 amino acids to be reliably determined 2. Immunoassays Illustrative non-limiting examples of immunoassays include, but are not limited to: immunoprecipitation; Western blot; ELISA; immunohistochemistry; immunocytochemistry; immunochromatography; flow cytometry; and, immuno-PCR. Polyclonal or monoclonal antibodies detectably labeled using various techniques known to those of ordinary skill in the art (e.g., colorimetric, fluorescent, chemiluminescent or radioactive labels) are suitable for use in the immunoassays.

Immunoprecipitation is the technique of precipitating an antigen out of solution using an antibody specific to that antigen. The process can be used to identify proteins or protein complexes present in cell extracts by targeting a specific protein or a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and optionally sorting microscopic particles or cells suspended in a stream of fluid. It allows simultaneous multi-parametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of a given gene fusion or other markers) into data of predictive value for a clinician. The clinician can access the predictive data using any suitable means. Thus, in some preferred embodiments, the present disclosure provides the further benefit that the clinician, who may not be specifically trained in genetics or molecular biology, need not understand the raw data. The data is can be presented directly to the clinician in its most useful form. The clinician is may then be then able to immediately utilize the information in order to optimize the care of the subject.

The present disclosure contemplates any method capable of receiving, processing, and transmitting the information to and from laboratories conducting the assays, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data may then be prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose, for example, further or altered intervention or counseling based on the results. In some embodiments, the data is used for research use. For example, the data may be used to further optimize the inclusion or elimination of markers as useful indicators of a particular condition or stage of disease.

E. In Vivo Imaging

The gene fusions of the present disclosure may also be detected using in vivo imaging techniques, including but not limited to: radionuclide imaging; positron emission tomography (PET); computerized axial tomography, X-ray or magnetic resonance imaging methods, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present disclosure are described below.

The in vivo imaging methods of the present disclosure are useful in the diagnosis of cancers that express the cancer markers of the present invention (e.g., breast cancer). In vivo imaging is used to visualize the presence of a marker indicative of the cancer. Such techniques allow for diagnosis without the use of an unpleasant biopsy. The in vivo imaging methods of the present disclosure are also useful for providing prognoses to cancer patients. For example, the presence of a marker indicative of cancers likely to metastasize can be detected. The in vivo imaging methods of the present disclosure can further be used to detect metastatic cancers in other parts of the body.

In some embodiments, reagents (e.g., antibodies) specific for the gene fusions of the present disclosure are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a gene fusion of the present disclosure). When active, it leads to a reaction that emits light. A CCD camera and software is used to capture the image and analyze it.

F. Compositions & Kits

Any of these compositions, alone or in combination with other compositions of the present disclosure, may be provided in the form of a kit. For example, the single labeled probe and pair of amplification oligonucleotides may be provided in a kit for the amplification and detection of gene fusions of the present invention. Kits may further comprise appropriate controls and/or detection reagents. The probe and antibody compositions of the present disclosure may also be provided in the form of an array.

Compositions for use in the diagnostic methods of the present invention include, but are not limited to, probes, amplification oligonucleotides, cDNAs obtained from gene fusion transcripts, and antibodies. Particularly preferred compositions detect a product only when a first gene fuses to a second gene. These compositions include: a single labeled probe comprising a sequence that hybridizes to the junction at which a 5' portion from a first gene fuses to a 3' portion from a second gene (i.e., spans the gene fusion junction); a pair of amplification oligonucleotides wherein the first amplification oligonucleotide comprises a sequence that hybridizes to a transcriptional regulatory region of a 5' portion from a first gene fuses to a 3' portion from a second gene; an antibody to an amino-terminally truncated protein resulting from a fusion of a first protein to a second gene; or, an antibody to a chimeric protein having an amino-terminal portion from a first gene and a carboxy-terminal portion from a second gene. Other useful compositions, however, include: a pair of labeled probes wherein the first labeled probe comprises a sequence that hybridizes to a transcriptional regulatory region of a first gene and the second labeled probe comprises a sequence that hybridizes to a second gene, probes and primers that span the fusion junction of a fusion generated by an internal deletion and antibodies that bind to amino acid sequences generated by internal deletions.

In some embodiments, compositions comprise any of the aforementioned compositions (e.g., probes, primers, or antibodies) bound to a target nucleic acid or polypeptide (e.g., complexes of reagents and targets).

IV. Drug Screening Applications/Companion Diagnostics

In some embodiments, the present disclosure provides drug screening assays (e.g., to screen for anticancer drugs). In some embodiments, the screening methods utilize cancer markers described herein. For example, in some embodiments, provided herein are methods of screening for compounds that alter (e.g., decrease) the expression of gene fusions. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present disclosure and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method.

In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, provided herein are screening methods for identifying modulators, i.e., candidate or test compounds or agents (e.g., proteins, peptides, peptidomimetics, peptoids, small molecules or other drugs) which bind to gene fusions of the present disclosure, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly breast cancer.

In one embodiment, the disclosure provides assays for screening candidate or test compounds that are substrates of a cancer marker protein or polypeptide or a biologically active portion thereof. In another embodiment, the disclosure provides assays for screening candidate or test compounds that bind to or modulate the activity of a cancer marker protein or polypeptide or a biologically active portion thereof.

The test compounds of the present disclosure can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a cancer marker mRNA or protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity, destruction or mRNA, or the like.

In some embodiments, the present disclosure provides compositions and methods for companion diagnostic assays. For example, in some embodiments, determining the presence or absence of a gene fusion in a sample from a subject is used to determine a treatment course of action (e.g., whether or not to administer a particular chemotherapy agent).

In some embodiments, the screening and diagnostic methods described herein find use in monitoring treatment (e.g., cancer treatment). For example, in some embodiments, subjects are assayed for the presence or absence of a fusion in a sample. A treatment is then provided. Following treatment, the diagnostic or screening assay is repeated to determine the presence or absence of a fusion. At this point, treatment can be altered, stopped, or started based on the presence or absence of fusion.

V. Transgenic Animals

The present disclosure contemplates the generation of transgenic animals comprising an exogenous cancer marker gene (e.g., gene fusion) of the present disclosure or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present disclosure find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present disclosure and are not to be construed as limiting the scope thereof.

Example 1

Methods
Clinical Study and Specimen Collection

Sequencing of clinical samples was performed under Institutional Review Board (IRB)-approved studies at the University of Michigan. Patients were enrolled and consented for integrative tumor sequencing, MI-ONCOSEQ (Michigan Oncology Sequencing Protocol, IRB# HUM00046018). Medically qualified patients 18 years or older with advanced or refractory cancer are eligible for the study. Informed consent details the risks of integrative sequencing and includes up-front genetic counseling. Biopsies were arranged for safely accessible tumor sites. Needle biopsies were snap frozen in OCT and a longitudinal section was cut. Hematoxylin and eosin (H&E) stained frozen sections were reviewed by pathologists to identify cores with highest tumor content. Remaining portions of each needle biopsy core were retained for nucleic acid extraction.

Cell Lines and Antibodies

Cell lines were purchased from the American Type Culture Collection (ATCC) or obtained from individual collections. Cells were grown in specified media supplemented with fetal bovine serum and antibiotics (Invitrogen). Anti-c-Myc antibody was purchased from Sigma. Anti-V5 antibody was purchased from Life Technologies. Anti-FGFR3 antibody was purchased from Epitomics. Anti-phospho-FGFR antibody was purchased from Cell Signaling.

DNA/RNA Isolation and cDNA Synthesis

Genomic DNA from frozen needle biopsies and blood was isolated using the Qiagen DNeasy Blood & Tissue Kit, according to the manufacturer's instructions. Total RNA was extracted from frozen needle biopsies using the Qiazol reagent with disruption using a 5 mm bead on a Tissuelyser II (Qiagen), and purified using a miRNeasy kit (Qiagen) with DNase I digestion, according to the manufacturer's instructions. Total RNA was isolated from cancer cell lines using the Trizol reagent (Life Technologies). RNA integrity was verified on an Agilent 2100 Bioanalyzer using RNA Nano reagents (Agilent Technologies). cDNA was synthesized from total RNA using SuperScript III (Invitrogen) and random primers (Invitrogen) for quantitative RT-PCR analysis.

Preparation of Next Generation Sequencing Libraries

Transcriptome libraries were prepared following Illumina's TruSeq RNA protocol, using 1-2 µg of total RNA. Poly(A)+ RNA was isolated using Sera-Mag oligo(dT) beads (Thermo Scientific) and fragmented with the Ambion Fragmentation Reagents kit (Ambion, Austin, Tex.). cDNA synthesis, end-repair, A-base addition, and ligation of the Illumina indexed adapters were performed according to Illumina's protocol. Libraries were size-selected for 250-300 bp cDNA fragments on a 3% Nusieve 3:1 (Lonza) agarose gel, recovered using QIAEX II gel extraction reagents (Qiagen), and PCR amplified using Phusion DNA polymerase (New England Biolabs) for 14 PCR cycles. The amplified libraries were purified using AMPure XP beads. Library quality was measured on an Agilent 2100 Bioanalyzer for product size and concentration. Paired end libraries were sequenced with the Illumina HiSeq 2000, (2×100 nucleotide read length). Reads that passed the chastity filter of Illumina BaseCall software were used for subsequent analysis.

Exome libraries of matched pairs of tumor/normal genomic DNAs were generated using the Illumina TruSeq DNA Sample Prep Kit, following the manufacturer's instructions. 3 µg of each genomic DNA was sheared using a Covaris S2 to a peak target size of 250 bp. Fragmented DNA was concentrated using AMPure XP beads (Beckman Coulter), followed by end-repair, A-base addition, and ligation of the Illumina indexed adapters according to Illumina's protocol. The adapter-ligated libraries were electrophoresed on 3% Nusieve 3:1 (Lonza) agarose gels and fragments between 300 to 350 bp were recovered using QIAEX II gel extraction reagents (Qiagen). Recovered DNA was amplified using Illumina index primers for 8 cycles. The amplified libraries were purified using AMPure XP beads and the DNA concentration was determined using a Nanodrop spectrophotometer. 1 µg of the libraries were hybridized to the Agilent SureSelect Human All Exon V4 at 65° C. for 60 hr following the manufacturer's protocol (Agilent). The targeted exon fragments were captured on Dynal M-280 streptavidin beads (Invitrogen), and enriched by amplification with the Illumina index primers for 9 additional cycles. After purification of the PCR products with AMPure XP beads, the quality and quantity of the resulting exome libraries were analyzed using an Agilent 2100 Bioanalyzer and DNA 1000 reagents.

The publicly available software FastQC was used to assess sequencing quality. For each lane, the per-base quality scores across the length of the reads were examined Lanes were deemed passing if the per-base quality score boxplot indicated that >75% of the reads had >Q20 for bases 1-80. In addition to the raw sequence quality, alignment quality was assessed using the Picard package. This allows monitoring of duplication rates and chimeric reads that may result from ligation artifacts; crucial statistics for interpreting the results of copy number and structural variant analysis.

Nomination of Gene Fusions

To identify gene fusions, paired-end transcriptome reads passing filter were mapped to the human reference genome and UCSC genes, allowing up to two mismatches, with Illumina ELAND software (Efficient Alignment of Nucleotide Databases) and Bowtie38. Sequence alignments were subsequently processed to nominate gene fusions using the method described earlier9. In brief, paired end reads were processed to identify those that either contained or spanned a fusion junction. Encompassing paired reads refer to those in which each read aligns to an independent transcript, thereby encompassing the fusion junction. Spanning mate pairs refer to those in which one sequence read aligns to a gene and its paired-end spans the fusion junction. Both categories undergo a series of filtering steps to remove false positives before being merged together to generate the final chimera nominations. Reads supporting each fusion were realigned using BLAT (UCSC Genome Browser) to reconfirm the fusion breakpoint.

Mutation Analyses

The resulting somatic mutations were annotated using RefSeq transcripts. HUGO gene names were used. The impact of coding non-synonymous amino acid substitutions on the structure and function of a protein was assessed using BLOSUM scores. It was also assessed whether the somatic variant was previously reported in dbSNP135 or COSMIC v5668. Tumor content for each tumor exome library was estimated from the sequence data by fitting a binomial mixture model with two components to the set of most likely SNV candidates on 2-copy genomic regions. The set of candidates used for estimation consisted of coding variants that (1) exhibited at least 3 variant fragments in the tumor sample, (2) exhibited zero variant fragments in the matched benign sample with at least 16 fragments of coverage, (3) were not present in dbSNP, (4) were within a targeted exon or within 100 base pairs of a targeted exon, (5) were not in homopolymer runs of four or more bases, and (6) exhibited no evidence of amplification or deletion. In order to filter out regions of possible amplification or deletion, coverage ratios were used to infer copy number changes, as described below. Resulting SNV candidates were not used for estimation of tumor content if the segmented log-ratio exceeded 0.2 in absolute value. Candidates on the Y chromosome were also eliminated because they were unlikely to exist in 2-copy genomic regions. Using this set of candidates, a binomial mixture model was fit with two components using the R package flexmix, version 2.3-8. One component consisted of SNV candidates with very low variant fractions, resulting from recurrent sequencing errors and other artifacts. The other component, consisting of the likely set of true SNVs, was informative of tumor content in the tumor sample. Specifically, under the assumption that most or all of the observed SNV candidates in this component are heterozygous SNVs, the estimated binomial proportion of this component were determined to represent one-half of the proportion of tumor cells in the sample. Thus, the estimated binomial proportion as obtained from the mixture model was doubled to obtain an estimate of tumor content.

Copy number aberrations were quantified and reported for each gene as the segmented normalized log 2-transformed exon coverage ratios between each tumor sample and matched normal sample (Lonigro, R. J. et al. Neoplasia 13, 1019-25 (2011)). To account for observed associations between coverage ratios and variation in GC content across the genome, lowess normalization was used to correct per-exon coverage ratios prior to segmentation analysis. Specifically, mean GC percentage was computed for each targeted region, and a lowess curve was fit to the scatterplot of log 2-coverage ratios vs. mean GC content across the targeted exome using the lowess function in R (version 2.13.1) with smoothing parameter f=0.05.

Somatic point mutations were identified in the tumor exome sequence data using the matched normal exome data to eliminate germline polymorphisms. Parameters and computational methods were as previously described (Grasso et al., Nature 487, 239 (2012).

For RNA-Seq gene expression analysis, transcriptome data was processed as previously described. Genes were nominated as exhibiting potential "outlier" expression relative to a cohort of N=282 previously sequenced tissues using the following conditions: (1) the gene was required to have an expression value of at least 20 RPKM in the sample of interest; (2) the gene was required to be at or above the 90th percentile relative to all previously sequenced tissues, of any type; (3) the gene was required to have a fold change of at least 2 relative to the maximum RPKM over all previously sequenced benign tissues; and (4) the 25th percentile of the gene expression measurements over the previously sequenced tissues was required to be less than 50 RPKM. Collectively, these parameters target genes with (1) high absolute expression, (2) high expression relative to previously sequenced tissues, (3) high expression relative to all benign tissues, and (4) expression that is not uniformly high across all tissues.

Partially redundant sequencing of areas of the genome affords the ability for cross validation of findings. Exome-based point mutation calls were cross-validated by manually examining the genomic and transcriptomic reads covering the mutation using the UCSC Genome Browser. Likewise, gene fusion calls from the transcriptome data can be further supported by structural variant detection in the genomic sequence data, as well as copy number information derived from the genome and exome sequencing.

Quantitative RT-PCR

For validation of fusion transcripts, quantitative RT-PCR assays were performed. Total cDNAs of index cases and negative control samples were synthesized using SuperScript III System according to the manufacturer's instructions (Invitrogen). Quantitative RT-PCR was performed using fusion-specific primers (Table 15) with SYBR Green Master Mix (Applied Biosystems) on the StepOne Real-Time PCR System (Applied Biosystems). The PCR products were further analyzed by agarose gel electrophoresis. Relative mRNA levels of the fusion transcripts were normalized to the expression of the housekeeping gene GAPDH. Inhibition of FGFR receptors and cell proliferation assay Bladder cancer cells SW780, J82, and HT1197 were seeded into 96-well plates in triplicate and allowed to attach before drug treatment. The FGFR inhibitor PD173074 (Selleck Chemicals) was added to the cultures at concentrations of 0, 5, 25, and 100 nM. Relative cell numbers were measured by WST-1 assays at indicated time points following the manufacturer's instructions (Roche).

Cloning and Expression of FGFR Fusions

The FGFR fusion alleles were PCR amplified from cDNA of the index cases of cell lines using the primers listed in Table 15 and the Expand High Fidelity protocol (Roche). The PCR product was digested with restriction endonuclease and ligated into the pcDNA3.1 vector (Invitrogen), which had been modified to contain a C-terminal MYC-epitope tag or V5-epitope tag. Expression constructs were transfected into HEK 293T cells using FuGene HD transfection reagent (Promega). Cells were harvested 24-hours post-transfection for protein lysate preparation.

For the cell proliferation assay, HEK 293T cells were transfected with control vector or FGFR fusion constructs. Twenty-four hours post-transfection, cells were trypsinized, resuspended in DMEM medium containing 2% FBS, and plated in quadruplicate at 12,000 cells per well in 24 well plates. The plates were incubated at 37° C. and 5% $CO_2$ atmosphere using the IncuCyte live-cell imaging system (Essen Biosciences). Cell proliferation was assessed by kinetic imaging confluence measurements at 3-hour time intervals.

Co-Immunoprecipitation

HEK 293T cells were grown to ~70% confluence in DMEM supplemented with 10% fetal bovine serum, followed by transfection with MYC-tagged or V5-tagged expression construct alone, or in combination using FuGene6 reagent (Promega). Twenty-four hours after transfection, cell pellets were lysed in lysis buffer (58 mM Na2HPO4, 17 mM $NaH_2PO_4$, 68 mM NaCl, 1% Triton X-100, 0.5% sodium deoxycholate, 0.1% SDS, and protease inhibitors), followed by immunoprecipitation with tag epitope-specific antibodies (Sigma) and protein-G Dynabeads (Invitrogen). Precipitates were washed three times with IP Wash buffer (20 mM Tris, pH8, 2 mM EDTA, 150 mM NaCl, 1% Triton X100) and eluted in SDS-PAGE loading buffer at 95° C. for 5 min Immunoprecipitated proteins were separated on SDS-PAGE and detected by Western blotting with tag epitope-specific antibodies (Sigma).

Mouse Xenograft Models

Five week-old male C.B17/SCID mice were procured from a breeding colony at University of Michigan, maintained by Dr. Kenneth Pienta. Mice were anesthetized using a cocktail of xylazine (80 mg/kg, intraperitoneal) and ketamine (10 mg/kg, intraperitoneal) for chemical restraint. Bladder cancer cells SW780 (2 million cells for each implantation site) or J82 (5 million cells for each implantation site) were resuspended in 100 μl of 1×PBS with 20% Matrigel (BD Biosciences) and were implanted subcutaneously into flank region on both sides. Eight mice were included in each experimental group. All tumors were staged for two weeks (SW780 cells) and three weeks (J82 cells) before starting the drug treatment. Xenografted mice with palpable tumors were treated with a FGFR inhibitor PD173074 (Selleck Chemicals) dissolved in 5% ethanol in corn oil (intraperitoneal). Mice in control group received 5% ethanol in corn oil as vehicle control. Tumor growth was recorded weekly by using digital calipers and tumor volumes were calculated using the formula $(\pi/6)$ (L×W2), where L=length of tumor and W=width. Any decrease in the body weight of mice was monitored bi-weekly during the course of the study. All experimental procedures involving mice were approved by the University Committee on Use and Care of Animals (UCUCA) at the University of Michigan and conform to their relevant regulatory standards.

Results

Four MI-ONCOSEQ patients were prospectively identified that harbored gene fusions of FGFR2 by transcriptome sequencing (FIG. 1). The first patient was a 34 year old female diagnosed with metastatic cholangiocarcinoma. By whole exome sequencing of the tumor relative to the matched normal, 8 nonsynonymous somatic point mutations were detected (Table 1). The most interesting of these in terms of tumor biology was the inactivation of the SWI/SNF chromatin remodeling complex through mutation of ARID1A (Q1573*) and PBRM1 (C736*). The SWI/SNF complex has been implicated as a tumor suppressor and inactivating somatic mutations of ARID1A and PBRM1 have been identified in renal cell carcinoma, breast, and ovarian cancer. The copy number landscape for a patient as determined by whole exome sequencing is shown in FIG. 1a and Table 2. An intrachromosomal fusion which resulted in the in frame fusion of the FGFR2 kinase to BICC1 (FIG. 1a) was detected. While 7 additional chimeric RNAs were detected (Table 3), only the FGFR2-BICC1 fusion exhibited a combination of high supporting reads (n=259), predicted in-frame fusion protein, and therapeutic actionability via kinase inhibition. The FGFR2-BICC1 fusion was confirmed by Q-PCR analysis (FIG. 1a).

Figure 2:
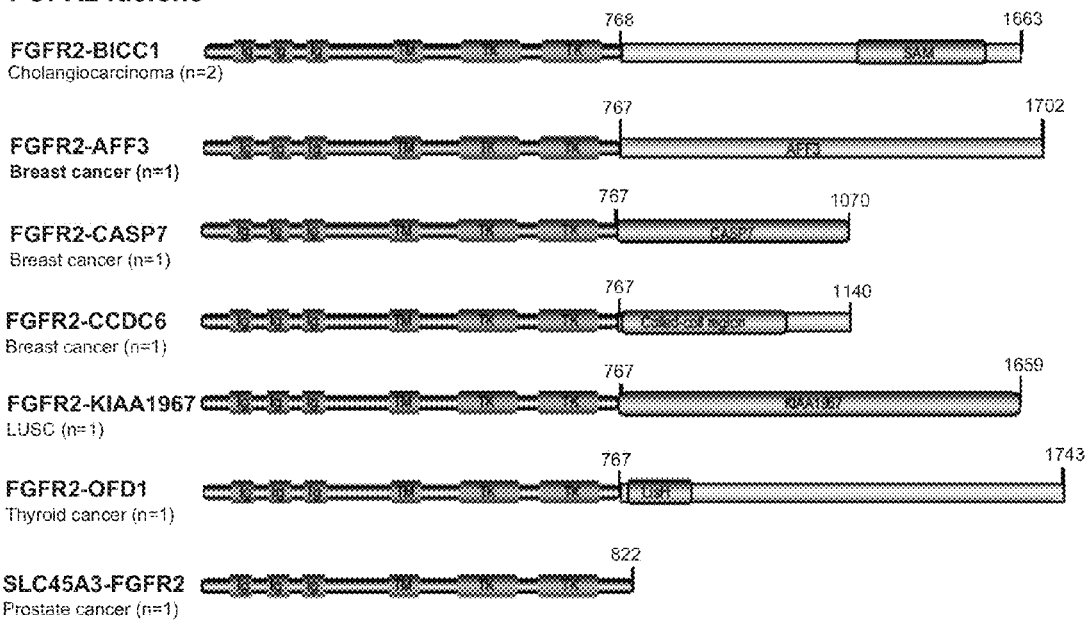
FIG. 2 shows schematic representations of the predicted FGFR gene fusions identified by transcriptome sequencing of human cancers. LUSC, Lung squamous cell carcinoma; HNSC, Head and Neck squamous cell carcinoma.
Figure 2:
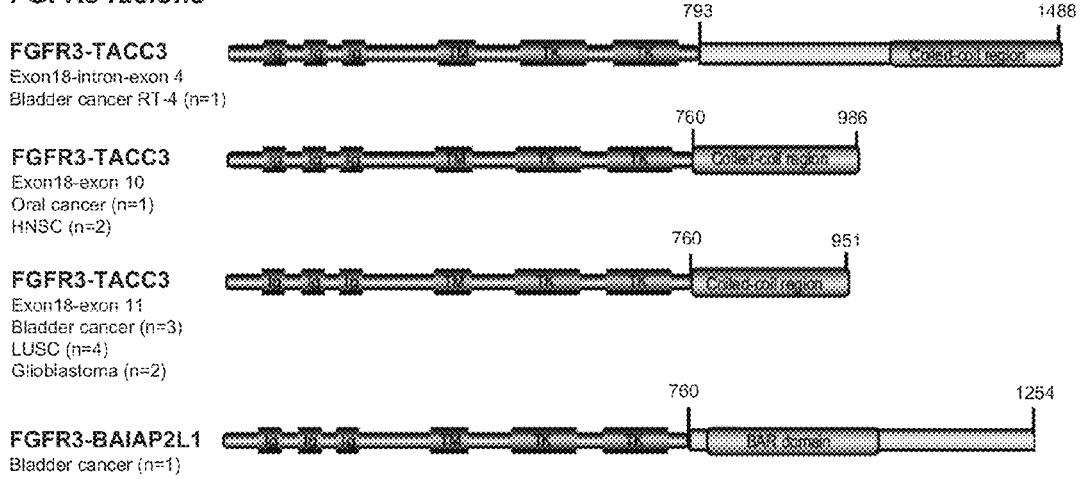
Figure 2:
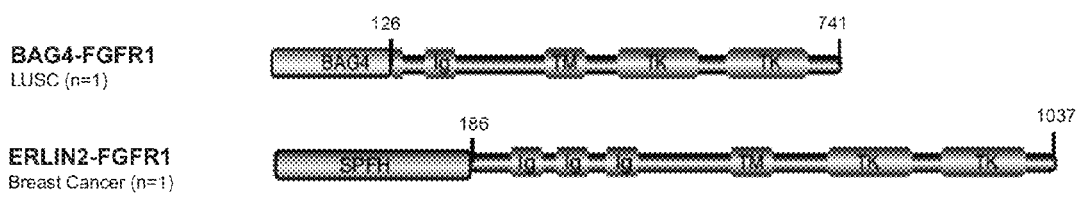

The second MI-ONCOSEQ patient with an FGFR2 fusion was a 61 year old male with metastatic cholangiocarcinoma. Like the first patient, this individual's tumor expressed an FGFR2-BICC1 fusion of identical configuration (FIG. 2b, Table 4). This fusion was similarly validated by Q-PCR (FIG. 2b). By contrast, however, this cholangiocarcinoma case exhibited 27 nonsynonymous somatic point mutations including an inactivating mutation of TP53 (R267W, Table 5) and a distinct copy number landscape (FIG. 2b, Table 6).

The third patient with an FGFR2 fusion identified was a 31 year old woman with metastatic breast cancer. RNA sequencing revealed an in frame interchromosomal fusion of FGFR2 with AFF3 which had a functional structure analogous to the FGFR2 kinase fusions found in cholangiocarcinoma (FIG. 1c). In addition to the FGFR2-AFF3 fusion, which was detected with 138 supporting reads and validated by Q-PCR (FIG. 1c), 6 additional gene fusions with a lower number of reads were identified (Table 7). This breast cancer case also harbored 204 nonsynonymous point mutations including mutation of TP53 (G199E) and a known activating mutation of PIK3CA (H1047R) (Table 8). While this breast cancer case exhibited a number of amplifications and deletions (Table 9), this patient was negative for the ERBB2 amplification.

The fourth patient with an FGFR2 fusion identified was a 57 year old male with Gleason score 5+4 metastatic prostate cancer. Transcriptome sequencing of a brain metastasis revealed an interchromosomal fusion of SLC45A3 with FGFR2 in which the SLC45A3 non-coding exon 1 is fused to the intact coding region of FGFR2 (FIG. 1d, Table 10). Since SLC45A3 is a prostate-specific, androgen regulated gene (Tomlins et al., Nature 448, 595 (2007), the SLC45A3-FGFR2 fusion is predicted to drive overexpression of wild type FGFR2. FGFR exhibited outlier expression in the index case relative to our compendium of prostate cancer tissues (n=84; FIG. 1d), and a similar rare case of FGFR2 outlier expression was identified in the Glinsky et al 20 prostate cancer cohort (FIG. 1).

It was next determined whether FGFR family fusions are present across carcinomas of different histologies. To address this RNAseq data generated from an internal cohort of diverse tumors (n=322) and The Cancer Genome Atlas (TCGA) effort (n=2053) was analyzed (Table 11) for gene fusions using several bioinformatics approaches (See Methods). Including the initial 4 index cases, 24 tumors or cell lines with FGFR1, 2 and 3 fusions (FIG. 2, Tables 12, 13, and 14) were identified. All of the gene fusions nominated expressed an FGFR family member as a 5' or 3' fusion partner with intact kinase domains indicating potential actionability. 5' FGFR fusions to BICC1, AFF3, CASP7, CCDC6, KIAA1967, OFD1, BAIAP2L1 and TACC3 (multiple exons) were identified and 3' FGFR fusions to SLC45A3, BAG4 and ERLIN2 were identified. Cancer types harboring FGFR fusions were quite diverse and included cholangiocarcinoma (n=2), breast cancer (n=4), prostate cancer (n=1), thyroid cancer (n=1), lung squamous cell carcinoma (n=6), bladder cancer (n=5), oral cancer (n=1), head and neck squamous cell carcinoma (n=2), and glioblastoma (n=2). FGFRs are known to exhibit tissue-specific splicing, resulting in IIIb and IIIc isoforms (Turner et al., Nat. Rev. cancer 10, 116 92010). Both IIIb and IIIc isoforms of FGFR2 and FGFR3 were evident in the RNA-seq data of the fusion cases, depending on cancer type (Table 12).

Figure 3:
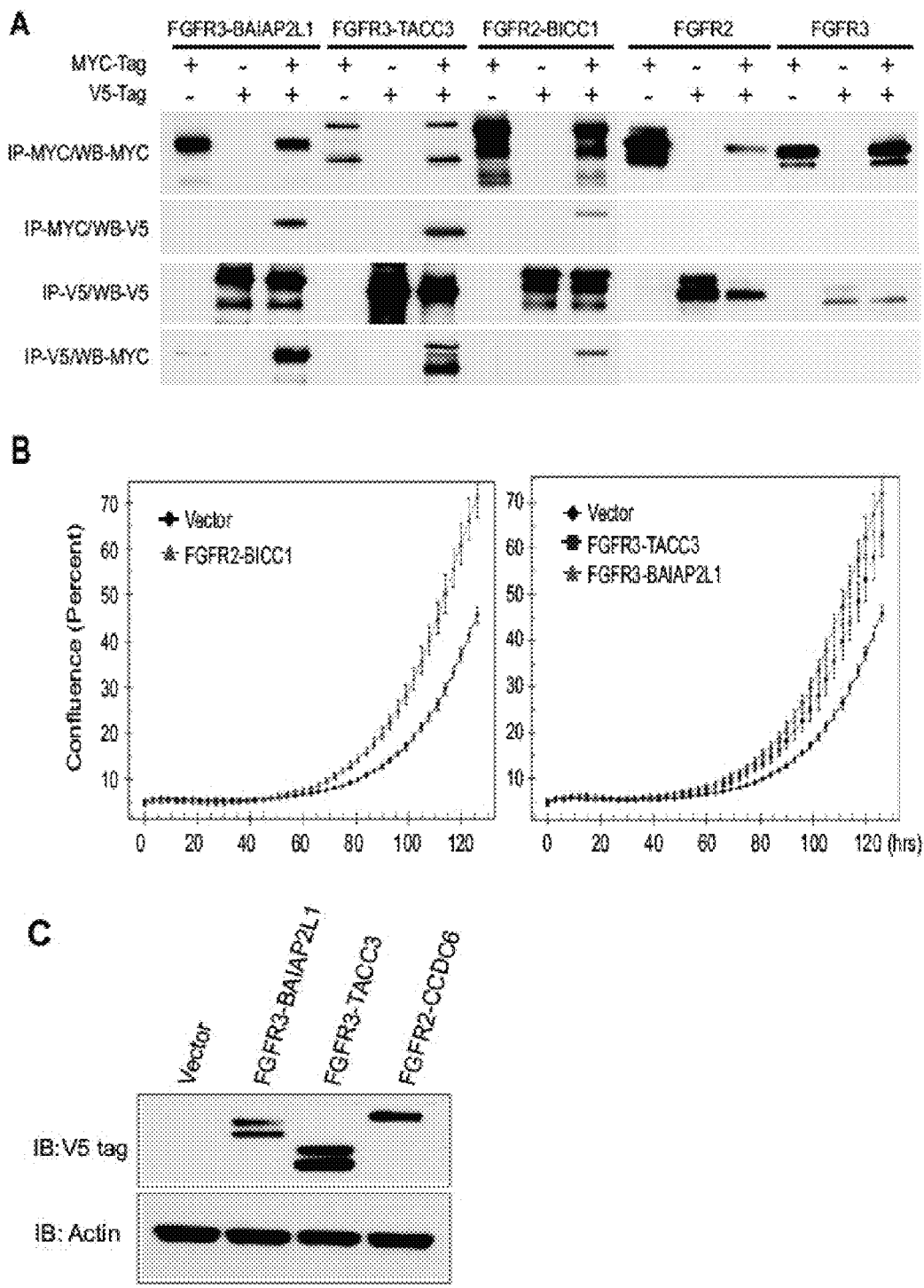
FIG. 3 shows characterization and functional analysis of the FGFR fusion proteins. a, Oligomerization of FGFR fusion proteins demonstrated by immunoprecipitation (IP)-Western Blotting (WB). b, Morphologic changes in 293T cells over-expressing FGFR fusion proteins. c, Cell proliferation assays as determined by live-cell imaging of 293T cells overexpressing various FGFR fusion proteins.
Figure 6:
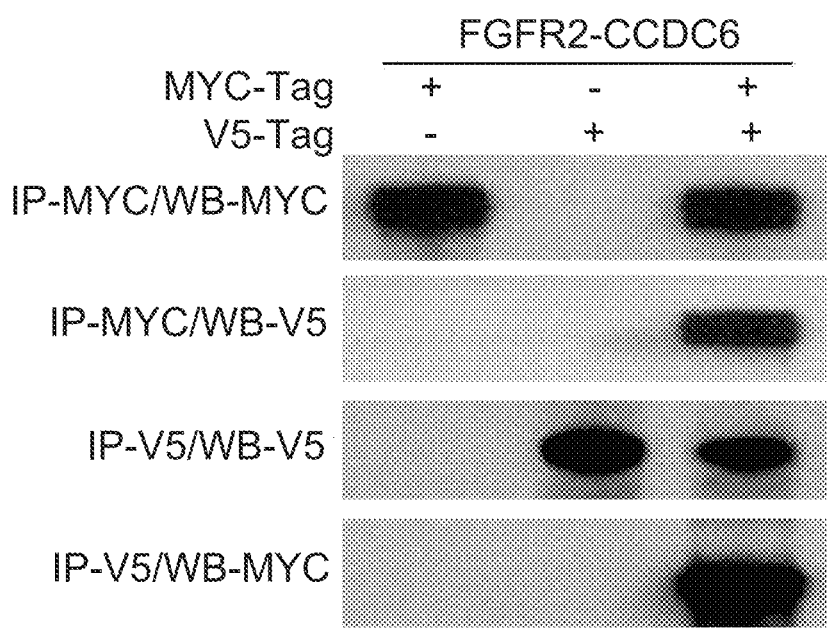
FIG. 6 shows dimerization of FGFR2-CCDC6 fusion proteins.
Figure 7:
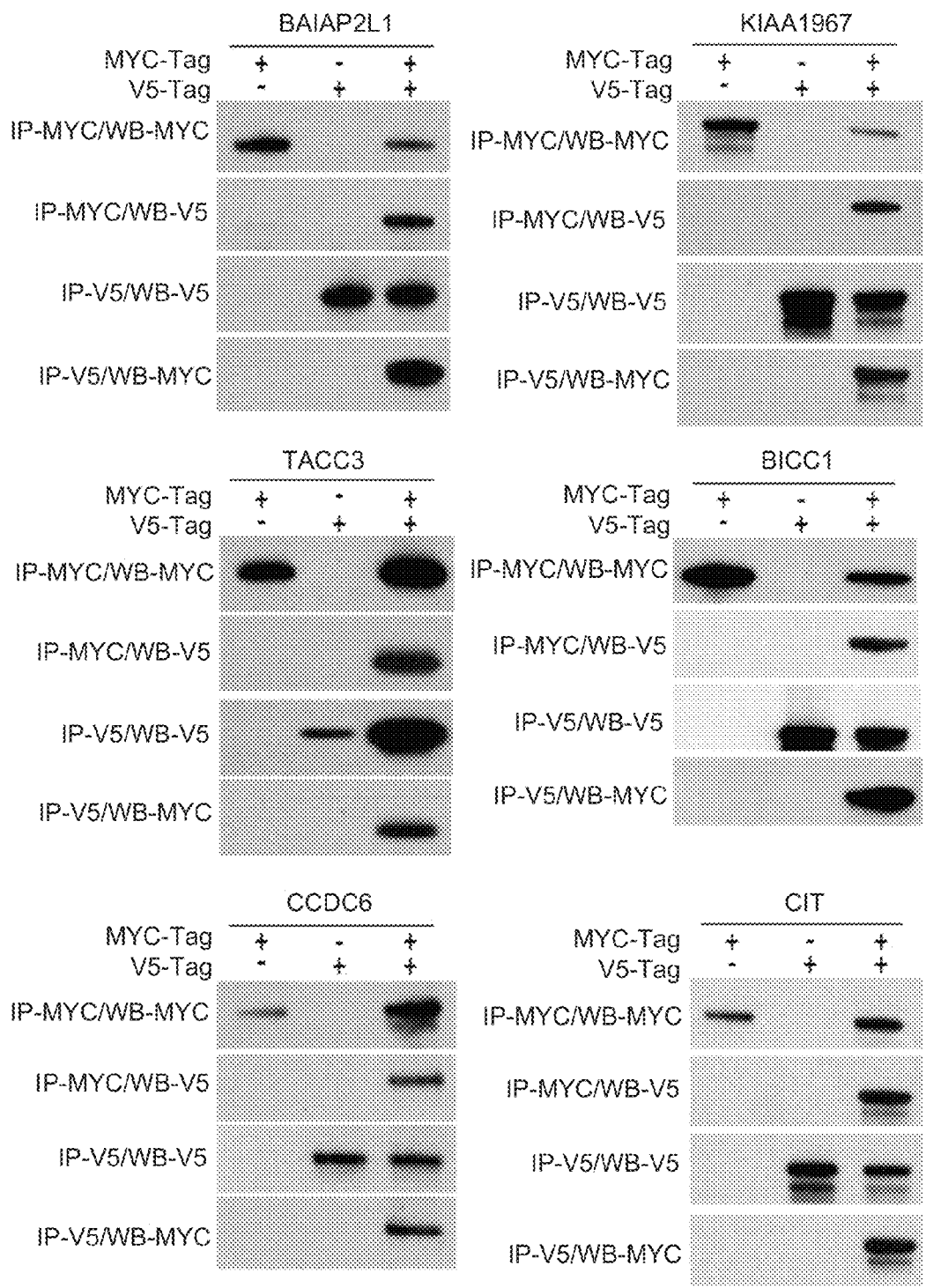
FIG. 7 shows dimerization of FGFR fusion partners.

As many of the expressed domains contributed by the diverse FGFR fusion partners have previously been suggested as dimerization motifs (Browman et al., Trends Cell Biol 17, 394-402 (2007); Chai, J. et al. Cell 107, 399-407 (2001); Ishizaki, T. et al. FEBS Lett 404, 118-24 (1997); Knight et al., Protein Sci 20, 1697-706 (2011); Mateja et al., J Mol Biol 357, 621-31 (2006); Peter, B. J. et al. Science 303, 495-9 (2004); Tong, Q. et al. Oncogene 10, 1781-7 (1995)), it was contemplated that oligomerization may serve as the common mechanism of activation of FGFR fusion proteins. Thus, selected epitope tagged versions of the FGFR fusions were expressed in HEK 293T cells protein oligomerization was assayed by co-immunoprecipitation. As examples, while FGFR3-BAIAP2L1, FGFR3-TACC3, FGFR2-BICC1, and FGFR2-CCDC6 interact in vitro, wild-type FGFR2 and FGFR3 do not in the absence of FGF ligands (FIG. 3a, FIG. 6). It was also shown that the isolated fusion domains provided by BAIAP2L1, TACC3, KIAA1967, CCDC6, and BICC1 interact in vitro as oligomerization domains (FIG. 7), further supporting the notion of oligomerization induced activation of FGFR kinase fusions.

Figure 4:
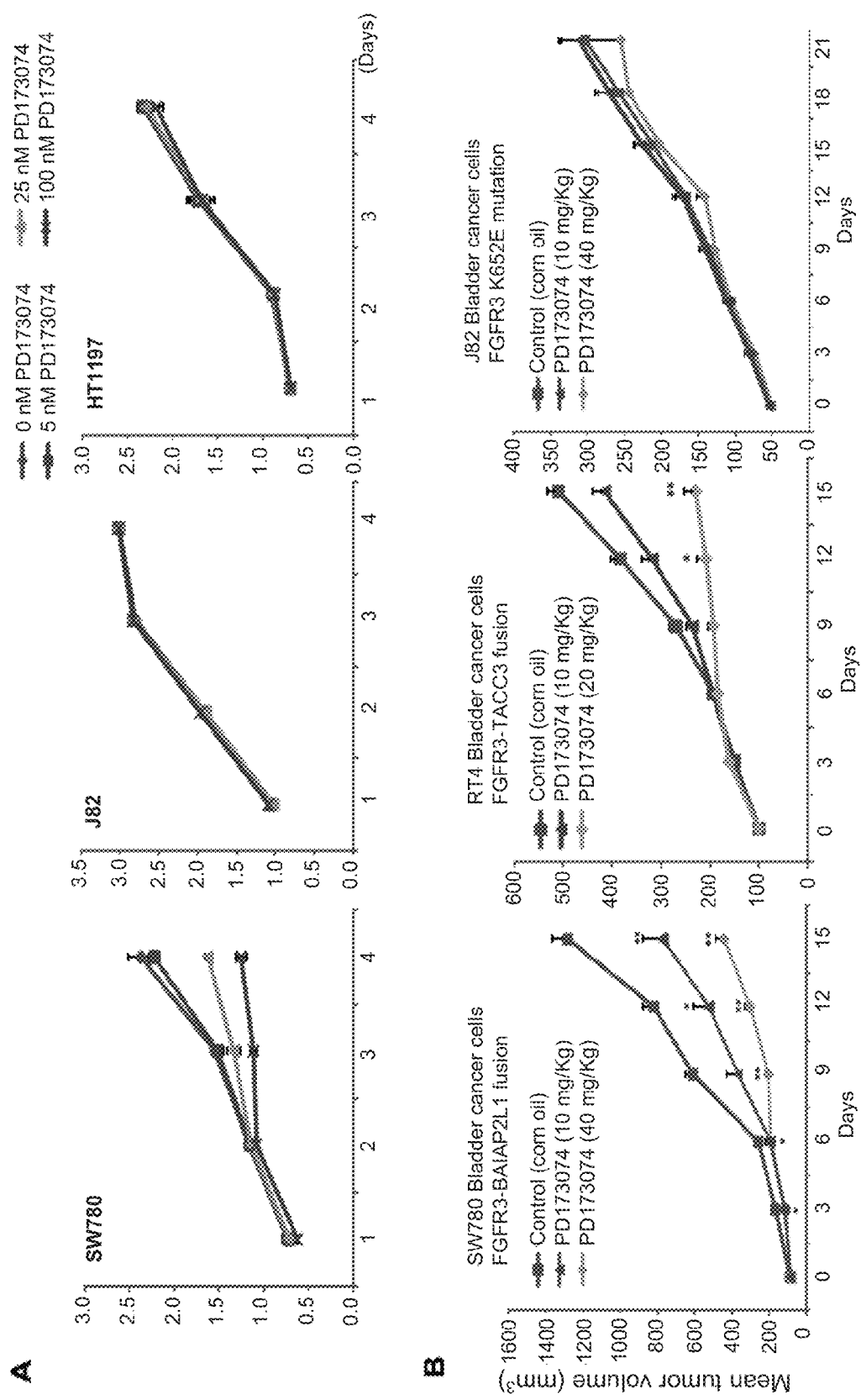
FIG. 4 shows differential sensitivity of FGFR fusion positive versus FGFR mutant bladder cancer xenograft growth to PD 173074.
Figure 4:
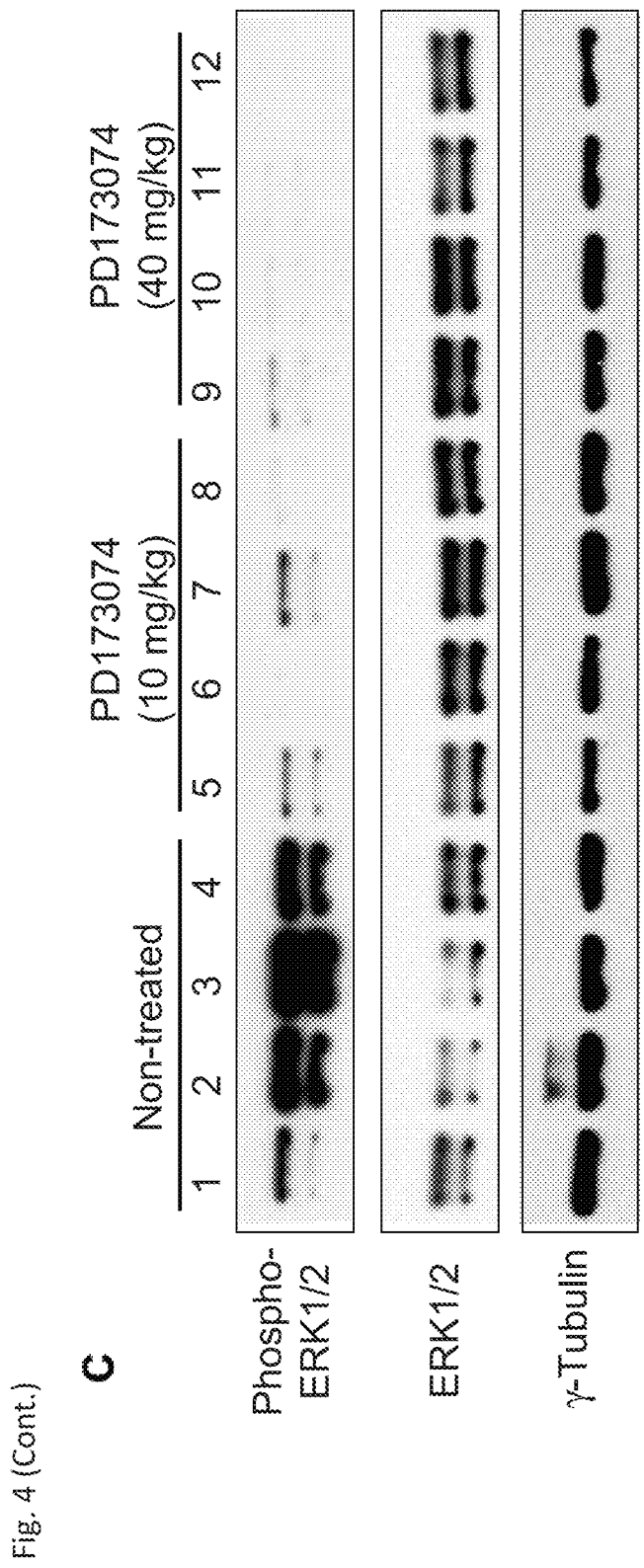
Figure 5:
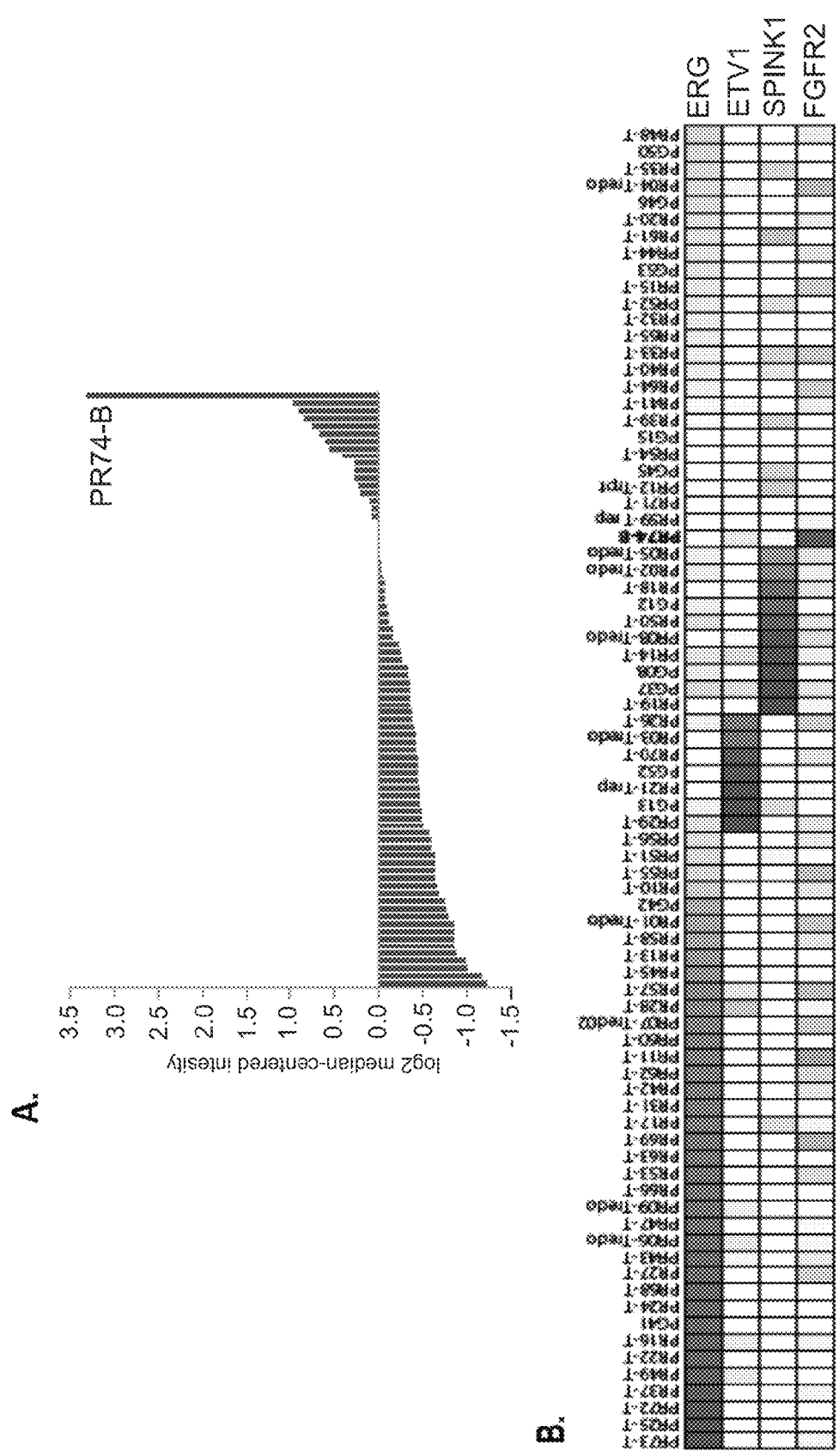
FIG. 5 shows rare FGFR2 outlier expression in an ETS fusion(-)/SPINK1(-) aggressive prostate cancer. A single localized PCa with outlier FGFR2 expression (PR74-B) was identified in the Glinsky et al. prostate profiling study. PR74-B was obtained from a 72 year old man with a Gleason score 9 PCa with extraprostatic extension on radical prostatectomy. b. Heatmap of ETS genes involved in recurrent fusions (ERG and ETV1), SPINK1 and FGFR2 in the Glinksky et al. study demonstrates that PR74-B is ETS fusion-/SPINK1-based on outlier expression.
Figure 8:
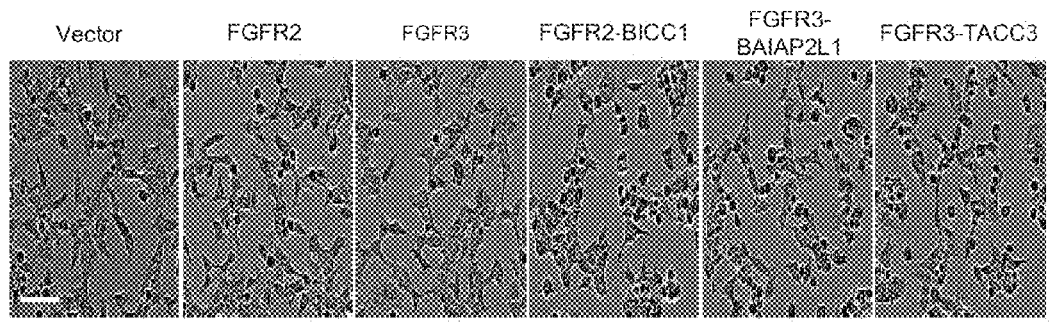
FIG. 8 shows morphologic changes in 293T cells over-expressing FGFR fusion proteins.
Figure 9:
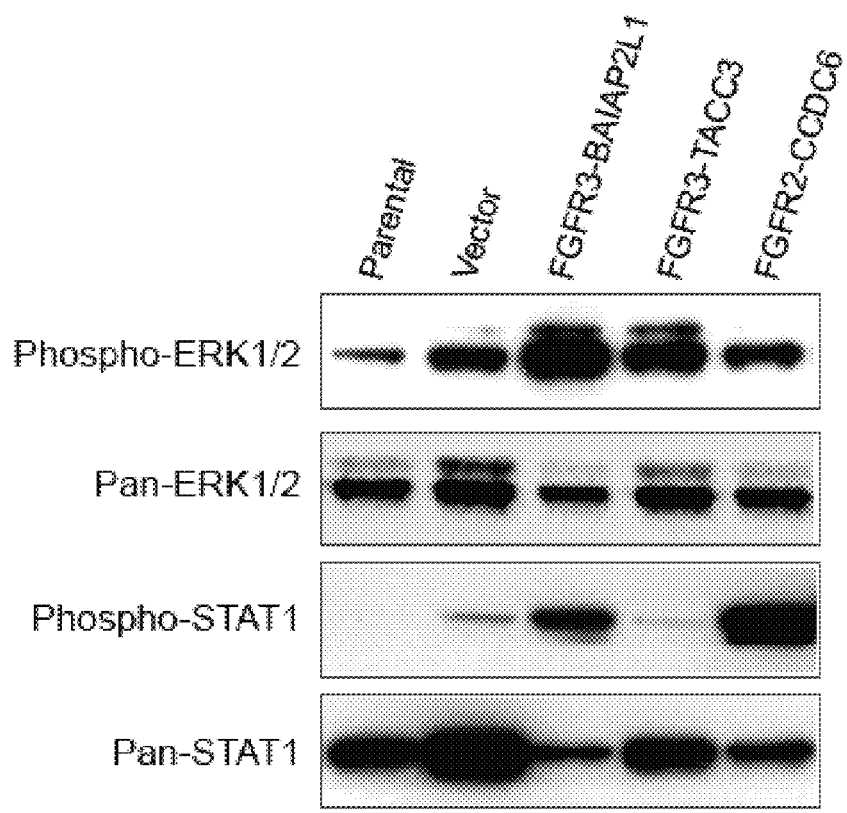
FIG. 9 shows activation of MAPK and STAT1 by FGFR fusion proteins in TERT-HME cells.
Figure 10:
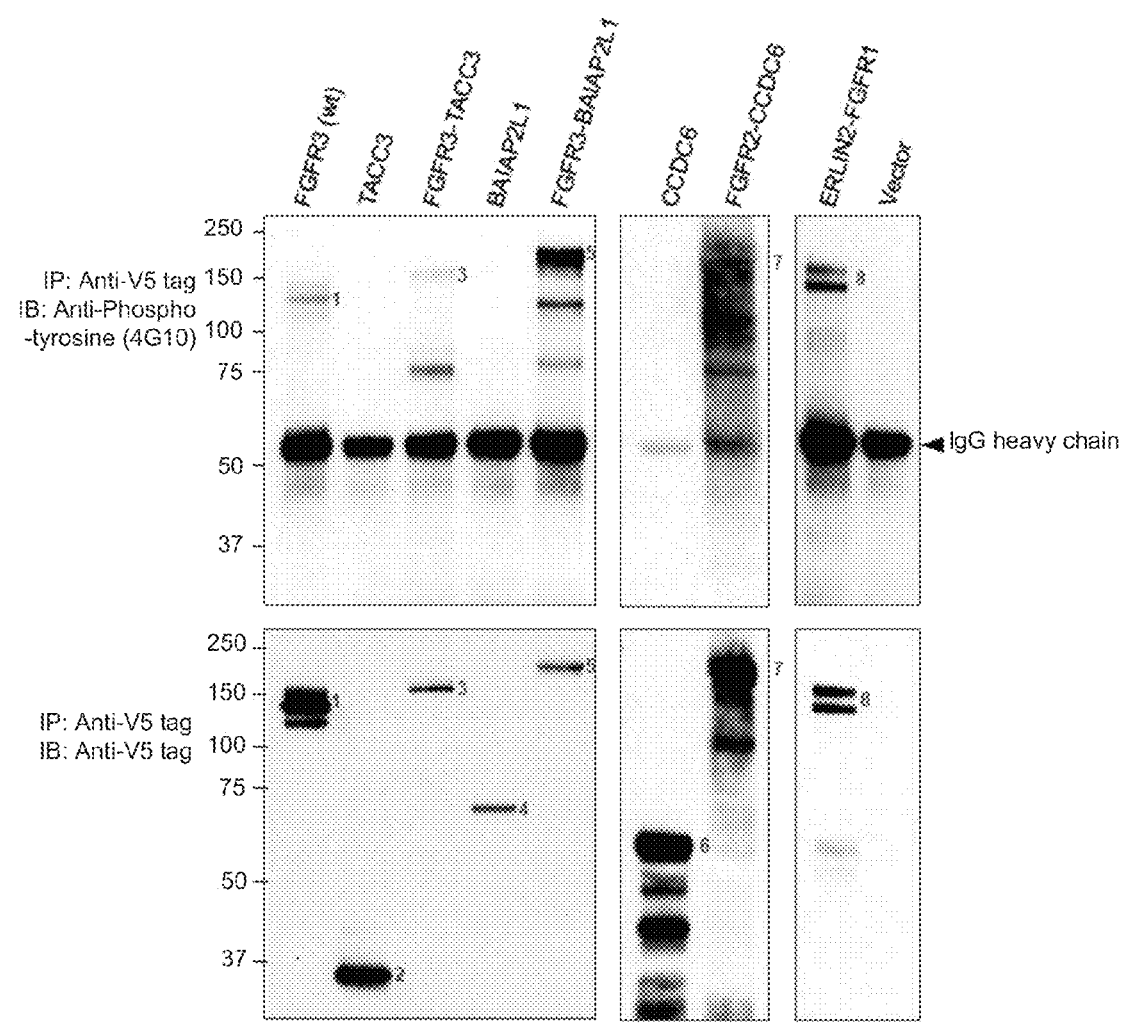
FIG. 10 shows detection of phosphorylated FGFR fusion proteins ectopically expressed in 293T cells.
Figure 11:
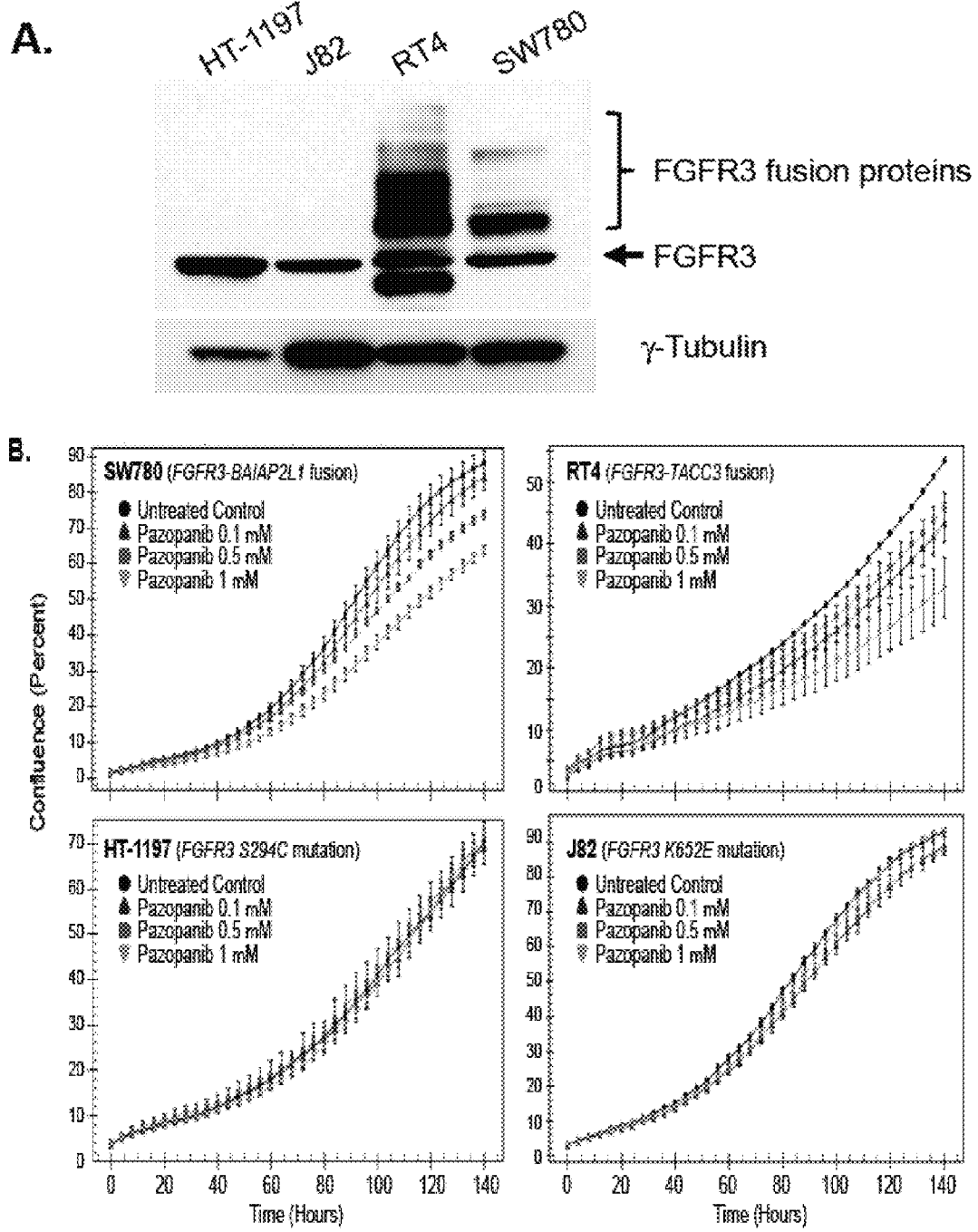
FIG. 11 shows detection of FGFR3 fusion proteins in bladder cancer cells SW780 (FGFR3-BAIAP2L1) and RT4 (FGFR3-TACC3) by Western blotting. B. Differential sensitivity of FGFR fusion positive versus FGFR mutant bladder cancer cell lines to FGFR inhibitor pazopanib. C. Effects of the FGFR inhibitor PD173074 on mouse body weight in xenograft models.
Figure 11:
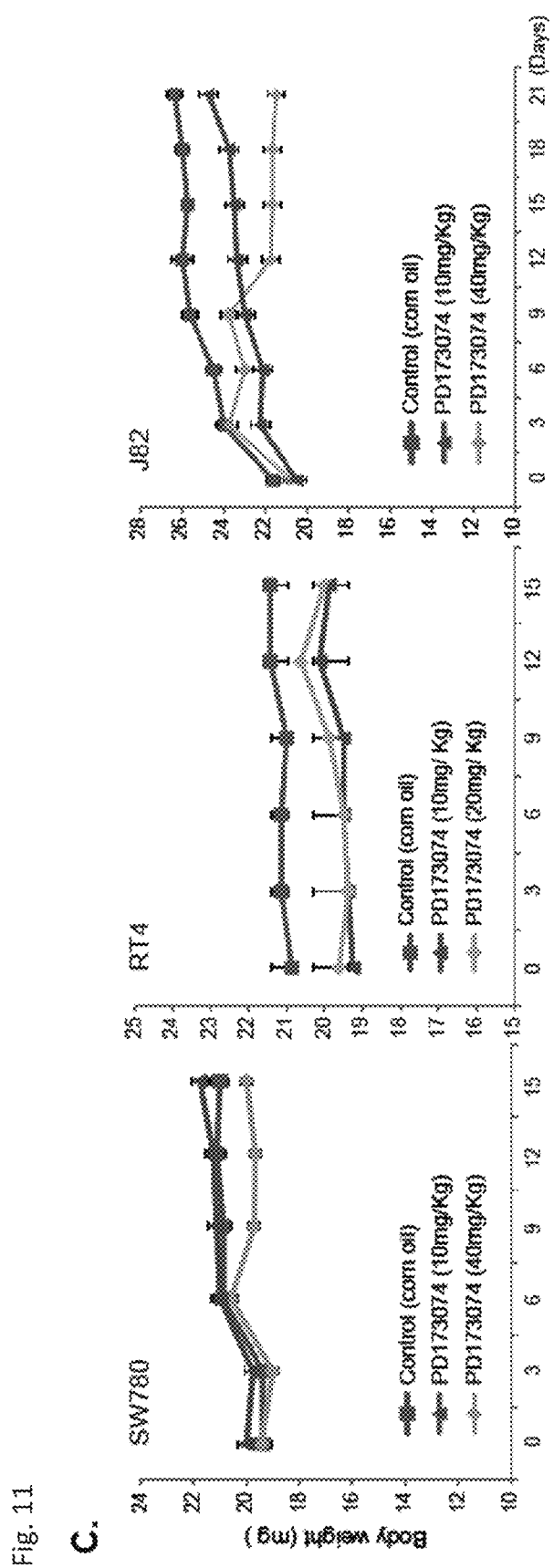
Figure 12:
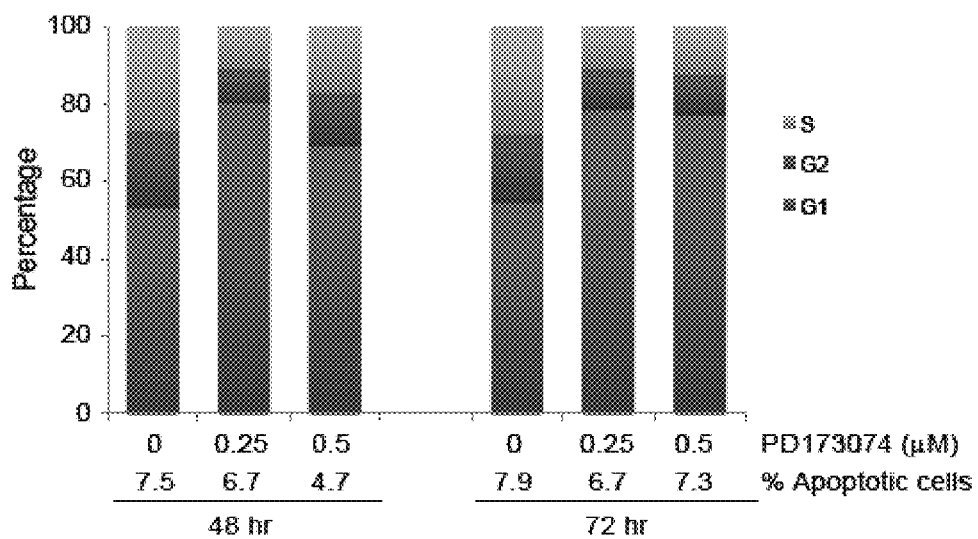
FIG. 12 shows flow cytometry analysis of bladder cancer cells treated with the FGFR inhibitor PD173074.
Figure 12:
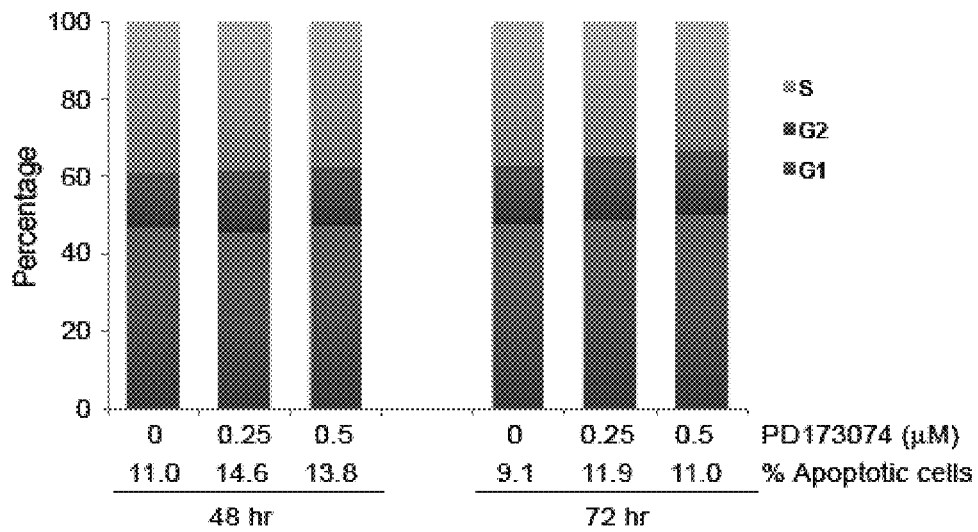
Figure 13:
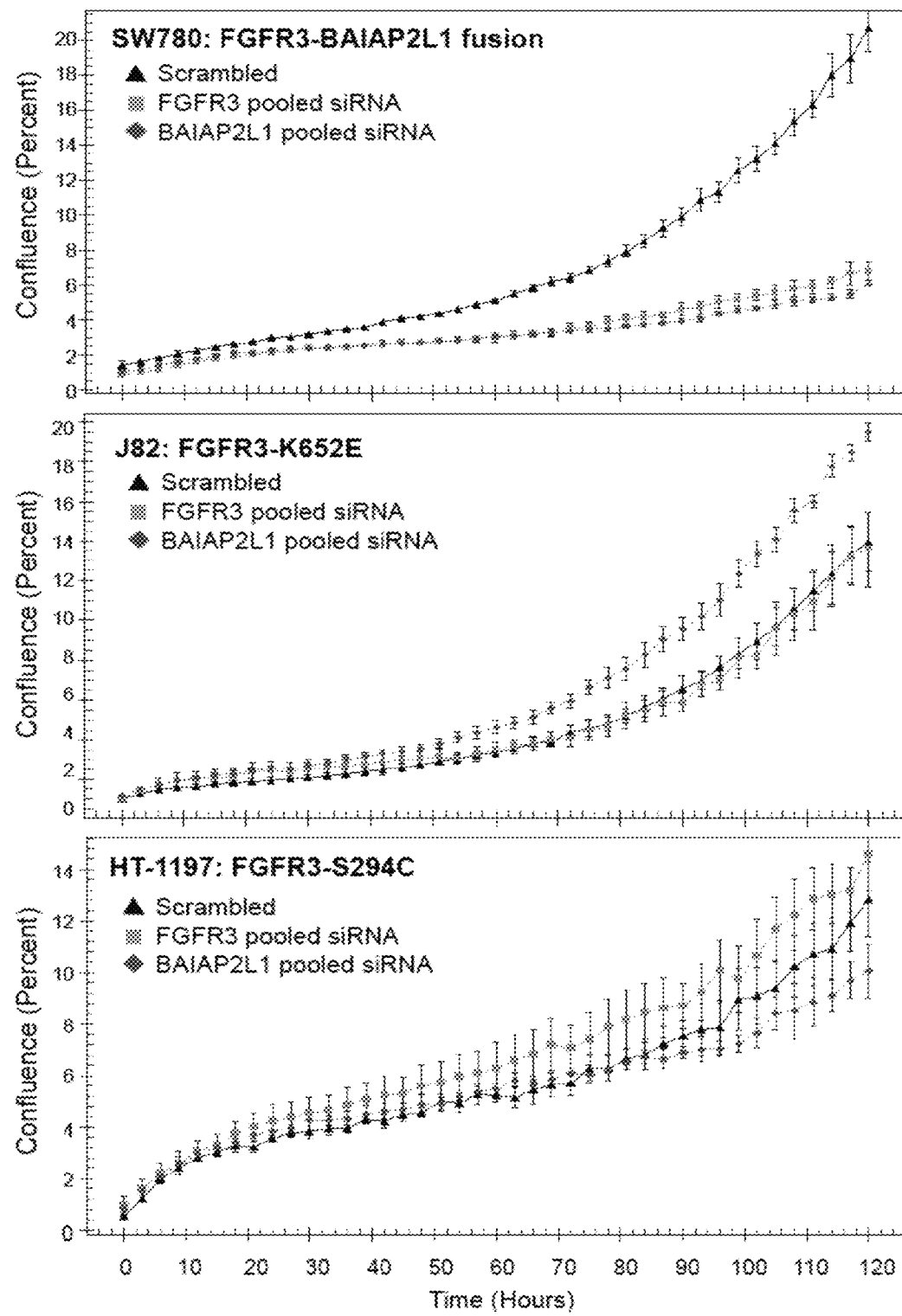
FIG. 13 shows that knockdown of FGFR3 or BAIAP2L1 reduces proliferation of SW780 cells.

Unlike wild-type FGFR2 and FGFR3, overexpression of selected examples of FGFR fusions including FGFR2-BICC1, FGFR3-BAIAP2L1, and FGFR3-TACC3 induced morphological changes characterized by rounding up of cells (FIG. 3b). Overexpression of these FGFR fusion proteins also enhanced cell proliferation based on real-time cell imaging (FIG. 3c). To evaluate the effects of pharmacologic inhibition of cells naturally harboring FGFR fusions, the sensitivity of bladder cancer cell lines to an FGFR small molecule kinase inhibitor, PD17307429 was assessed. SW780 cells were characterized to have a fusion of FGFR3-BAIAP2L1 in this study (FIG. 4a) while J82 and HT-1197 cells harbor activating point mutations of FGFR3 (K652E and S249C respectively (Miyake et al., J Pharmacol Exp Ther 332, 795-802 (2010)), COSMIC). While the FGFR fusion cell line SW780 was sensitive to nanomolar concentrations of PD173074, the FGFR3 mutant cell lines were not (FIG. 3d) indicating that FGFR fusions may exhibit exquisite sensitivity to FGFR inhibitors. These data were recapitulated in vivo as SW780 xenografts exhibited decreased tumor growth based on increasing doses of PD173074 while J82 xenografts did not (FIG. 4). Toxicity of PD173074 was also monitored by assessing mouse body weight (FIG. 8b).

Sequencing and analysis of each of the four FGFR fusion patients described in this study was carried out in a time frame of 5 to 7 weeks. The first cholangiocarcinoma patient, who harbored the FGFR2-BICC1 fusion, underwent a conventional chemotherapy regimen in which her cancer progressed and chose not to pursue FGFR directed therapy and died 3 months after enrollment on this protocol. The second cholangiocarcinoma patient, also harboring an FGFR2-BICC1 fusion underwent conventional chemotherapy but did not show tumor shrinkage and was enrolled on an FGFR inhibitor clinical trial.

Activating point mutations of FGFR1, FGFR2, FGFR3 or FGFR4 have been identified in a variety of cancers including gliomas, bladder cancer, multiple myeloma, and rhabdomyosarcomas (Wesche et al., Biochem J 437, 199-213 (2011)). Studies of hematological diseases led to the identification of 3' gene fusions of FGFR1 in myeloproliferative disorder (Jackson et al., Hum Pathol 41, 461-76 (2010)) and 3' FGFR3 fusions in peripheral T-cell lymphoma (Yagasaki, F. et al. Cancer Res 61, 8371-4 (2001)) and multiple myeloma (Jackson et al., Hum Pathol 41, 461-76 (2010)). As described earlier, 5' gene fusions of FGFR1 and FGFR3 with TACC1 and TACC3 have previously been identified in GBM (Singh, D. et al. Science 337, 1231-5 (2012)). Experiments described above identified potentially actionable 5' and 3' FGFR rearrangements across a diverse array of both common and rare solid tumors. Ten novel FGFR fusion partners were identified. In the Singh et al study, the mechanism of activation of the FGFR fusions is proposed to be through mis-localization to mitotic spindle poles mediated by the coiled-coil domain of TACC fusion partner (Singh, D. et al. Science 337, 1231-5 (2012)). This presumably leads to mitotic and chromosomal segregation defects triggering aneuploidy.

The present invention is not limited to a particular mechanism. Indeed, an understanding of the mechanism is not necessary to practice the present invention. Nonetheless, it is contemplated that the FGFR fusion partners (e.g., BICC1, TACC3, CCDC6, BAIAP2L1, KIAA1967, CASP7, and OFD1) mediate oligomerization, which triggers activation of the respective FGFR kinase.

The SLC45A3-FGFR2 gene fusion identified in the index prostate cancer exhibits a pathogenic role distinct from fusion protein oligomerization (shared by the other gene fusions tested). The entire open reading frame of FGFR2 is expressed under the control of an androgen-regulated promoter of SLC45A3, leading to the marked overexpression of FGFR2. Another observation in this study is the enhanced sensitivity to the FGFR inhibitor PD 173074 of cell lines harboring an FGFR3 fusion relative to those that have an activating point mutation of FGFR3. Clinical trials for several FGFR inhibitors are underway or in late stage pre-clinical development (Brooks et al., Clin Cancer Res 18, 1855-62 (2012); Greulich, H. & Pollock, P. M. Trends Mol Med 17, 283-92 (2011); Guagnano, V. et al. Cancer Discov (2012)). The wide range of cancers in which FGFR rearrangements were detected in this study indicates that development of FGFR rearrangements are lineage independent and emphasizes the importance of developing mutation enriched clinical trials rather than trials based on tissue of origin.

This study identified 4 patients with FGFR family gene fusions through an established clinical sequencing project called MI-ONCOSEQ (the Michigan Oncology Sequencing Program). Combining these index patients with an analysis of transcriptome data from the internal tumor cohorts as well as the TCGA identified FGFR fusions in a wide array of cancers including cholangiocarcinoma, GBM, squamous lung cancer, bladder cancer, breast cancer, thyroid cancer, oral cancer, head and neck squamous cell carcinoma, and prostate cancer. In addition to TACC1 and TACC3 10 additional FGFR fusion partners as well as implicated 3 out 4 FGFR family members (FGFR1, 2, and 3) were identified in gene rearrangements.

TABLE 1

| SAMPLE | GENE | LOC (hg18) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1036 | ARID1A | chr1:26974022 | C | T | 38 | 110 | 0.35 | Q1576* | −4 | 9.2 |
| MO_1036 | LRRC24 | chr8:145719484 | A | G | 112 | 276 | 0.41 | L242P | −3 | 9.0 |
| MO_1036 | PBRM1 | chr3:52618728 | A | T | 47 | 115 | 0.41 | C736* | −4 | 2.4 |
| MO_1036 | GFRA1 | chr10:117846228 | C | T | 17 | 69 | 0.25 | E265K | 1 | 0.7 |
| MO_1036 | MADCAM1 | chr19:452701 | G | A | 7 | 28 | 0.25 | D234N | 1 | 0.3 |
| MO_1036 | ROR2 | chr9:93526123 | T | A | 25 | 163 | 0.15 | Q825L | −2 | 0.2 |
| MO_1036 | OR51D1 | chr11:4618548 | A | G | 95 | 236 | 0.40 | M318V | 1 | 0.0 |
| MO_1036 | RPL3L | chr16:1944012 | C | T | 29 | 107 | 0.27 | G48S | 0 | 0.0 |

TABLE 2

| Sample | Segment (hg18) | Genes in this region | Span (bp) | Number of exons | Copy number ratio (gains) |
|---|---|---|---|---|---|
| MO_1036 | chr18: 12874154-12938146 | PTPN2, SEH11 | 63,992 | 2 | 3.74 |
| MO_1036 | chr11:63709893-63710241 | STIP1 | 348 | 2 | 3.10 |
| MO_1036 | chr19:4408610-4423383 | UBXN6, HDGF2 | 14,773 | 2 | 3.08 |
| MO_1036 | chr5:10303134-10303443 | CCT5 | 309 | 2 | 2.40 |
| MO_1036 | chr6:26128947-26325246 | HFE, HIST1H3A, HIST1H4A, HIST1H4B | 196,299 | 35 | 1.57 |
| MO_1036 | chr12:9639140-10265625 | LOC374443, CLEC2D/2B/L1, CD69, KLRF1 | 626,485 | 95 | 1.56 |
| MO_1036 | chr18:16944866-20311136 | RIOK3, ROCK1 | 3,366,270 | 331 | 1.53 |
| MO_1036 | chr13:27417497-30093937 | CDX2, FLT1, FLT3 | 2,676,440 | 142 | 1.51 |
| MO_1036 | chr13:32911844-33438270 | STARD13, RFC3 | 526,426 | 12 | 1.48 |
| MO_1036 | chr12:78680-9468534 | CCND2, DYRK4, KDM5A, WNK1, ZNF384 | 9,389,854 | 1212 | 1.47 |

TABLE 3

| Sample | 5' Gene | 3' Gene | Number of Supporting Reads | Type |
|---|---|---|---|---|
| MO_1036 | CDC42SE2 | DNMT2 (TRDMT1) | 515 | Interchromosomal |
| MO_1036 | FGFR2 | BICC1 | 259 | Intrachromosomal |
| MO_1036 | ALS2CR16 | ALS2CR8 | 111 | Intrachromosomal |
| MO_1036 | uc003sbm (MSH5) | NFKBIL1 | 17 | Intrachromosomal |
| MO_1036 | LPCAT3 | C1RL | 15 | Intrachromosomal |
| MO_1036 | FAM114A2 | CDC42SE2 | 11 | Intrachromosomal |
| MO_1036 | CDC42SE2 | TRDMT1 | 9 | Interchromosomal |
| MO_1036 | THRAP3 | STK40 | 4 | Intrachromosomal |

TABLE 4

| Sample | 5' Gene | 3' Gene | Number of Supporting Reads | Type |
|---|---|---|---|---|
| MO_1039 | FGFR2 | BICC1 | 83 | Intrachromosomal |
| MO_1039 | LDB1 | BICC1 | 30 | Intrachromosomal |
| MO_1039 | FAM62A | LOC728937 | 20 | Intrachromosomal |
| MO_1039 | GLG1 | GRM5 | 14 | Interchromosomal |
| MO_1039 | AIFM1 | FGF13 | 3 | Intrachromosomal |

TABLE 5

| SAMPLE | GENE | LOC (hg18) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1039 | EEF1D | chr8:144743100 | C | T | 33 | 175 | 0.19 | A99T | 0 | 105.1 |
| MO_1039 | GMAS | chr20:56862022 | C | T | 66 | 173 | 0.38 | P103S | −1 | 69.1 |
| MO_1039 | GNAS | chr20:56862021 | G | A | 68 | 175 | 0.39 | M102I | 1 | 69.1 |
| MO_1039 | RNF130 | chr5:179372696 | T | A | 38 | 105 | 0.36 | R222W | −3 | 40.6 |
| MO_1039 | PRPF3 | chr1:148572293 | C | A | 61 | 215 | 0.28 | P243T | −1 | 39.4 |
| MO_1039 | NFE2L2 | chr2:177807205 | T | C | 38 | 88 | 0.43 | D29G | −1 | 30.0 |
| MO_1039 | IRF2BP1 | chr19:51080358 | G | A | 83 | 205 | 0.40 | S172F | −2 | 20.1 |
| MO_1039 | GPT | chr8:145702753 | A | G | 33 | 106 | 0.31 | N398S | 1 | 19.9 |
| MO_1039 | TP53 | chr17:7517864 | G | A | 50 | 83 | 0.60 | R267W | −3 | 19.2 |
| MO_1039 | PRODH2 | chr19:40982805 | G | A | 17 | 66 | 0.26 | P529L | −3 | 9.6 |
| MO_1039 | NASP | chr1:45852427 | A | C | 15 | 61 | 0.25 | I529L | 2 | 8.9 |
| MO_1039 | IPO7 | chr11:9416221 | G | A | 19 | 41 | 0.46 | M836I | 1 | 8.6 |
| MO_1039 | ZBTB33 | chrX:119271861 | C | A | 6 | 30 | 0.20 | S188Y | −2 | 7.6 |
| MO_1039 | BCOR | chrX:39807134 | G | C | 50 | 71 | 0.70 | Q1294E | 2 | 6.1 |
| MO_1039 | YARS2 | chr12:32799976 | C | A | 58 | 146 | 0.40 | G34C | −3 | 5.7 |
| MO_1039 | PDE4DIP | chr1:143626918 | G | A | 10 | 35 | 0.29 | R622* | −4 | 5.0 |
| MO_1039 | EPHB3 | chr3:185773007 | G | A | 37 | 99 | 0.37 | D69N | 1 | 4.8 |

TABLE 5-continued

| SAMPLE | GENE | LOC (hg18) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1039 | KIAA1199 | chr15:78968899 | A | C | 31 | 68 | 0.46 | K333Q | 1 | 2.2 |
| MO_1039 | RIC8B | chr12:105778179 | A | T | 6 | 25 | 0.24 | D437V | −3 | 2.2 |
| MO_1039 | SPAG1 | chr8:101275567 | G | A | 33 | 53 | 0.62 | E331K | 1 | 1.8 |
| MO_1039 | SHROOM4 | chrX:50394164 | G | T | 97 | 146 | 0.66 | T550K | −1 | 0.5 |
| MO_1039 | CDKL5 | chrX:1852688 | G | A | 118 | 184 | 0.64 | E575K | 1 | 0.1 |
| MO_1039 | EMR3 | chr19:14609990 | C | T | 56 | 141 | 0.40 | G471S | 0 | 0.1 |
| MO_1039 | KCNA10 | chr1:110861676 | C | T | 50 | 171 | 0.29 | M419I | 1 | 0.1 |
| MO_1039 | FAM19A4 | chr3:68884793 | C | T | 25 | 104 | 0.24 | R66H | 0 | 0.0 |
| MO_1039 | PRDM9 | chr5:23558241 | G | C | 7 | 69 | 0.10 | V194L | 1 | 0.0 |
| MO_1039 | CSRNP1 | chr3:3916733 | C | T | 11 | 54 | 0.20 | R75Q | 1 | NA |

TABLE 6

| Sample | Segment (hg18) | Genes in this region | Span (bp) | Number of exons | Copy number ratio (gains) |
|---|---|---|---|---|---|
| MO_1039 | chr1:153098887-153716609 | CLK2, MUC1 | 617,722 | 220 | 3.61 |
| MO_1039 | chr1:144963163-145553014 | BCL9 | 589851 | 47 | 2.89 |
| MO_1039 | chr1:153757794-161591884 | DDR2, FCGR2B, INSRR, NTRK1, PRCC, SDHC, UHMK1 | 7,834,090 | 1244 | 2.89 |
| MO_1039 | chr1:148124359-150554432 | ARNT | 2430073 | 561 | 2.86 |
| MO_1039 | chr1:150649330-152976224 | NPR1, TPM3 | 2,326,894 | 388 | 2.83 |
| MO_1039 | chr1:145554338-145882120 | BCL9 | 327,782 | 17 | 2.20 |
| MO_1039 | chr20:30074126-30126201 | HCK | 52,075 | 12 | 2.15 |
| MO_1039 | chr1:150589796-150597931 | FLG2 | 8,135 | 12 | 2.12 |
| MO_1039 | chr1:152994932-153061274 | KCNN3 | 66,342 | 5 | 2.12 |
| MO_1039 | chr16:69441206-69754032 | HYDIN | 312,826 | 72 | 1.97 |
| MO_1039 | chr1:162512589-162795748 | PBX1 | 283,159 | 2 | 1.96 |

| Sample | Segment (hg18) | Genes in this region | Span (bp) | Number of exons | Copy number ratio (losses) |
|---|---|---|---|---|---|
| MO_1039 | chr6:168856780-168857712 | — | 932 | 3 | 0.37 |
| MO_1039 | chr8:935432-947796 | ERICH1-AS1 | 12,364 | 2 | 0.38 |
| MO_1039 | chr21:9809235-9815818 | — | 6,583 | 3 | 0.50 |
| MO_1039 | chr10:38835211-39184276 | ACTR3BP5 | 349,065 | 3 | 0.52 |
| MO_1039 | chr6:74228416-74285712 | MTO1, EEF1A1 | 57,296 | 18 | 0.57 |

TABLE 7

| Sample | 5' Gene | 3' Gene | Number of Supporting Reads | Type |
|---|---|---|---|---|
| MO_1051 | FGFR2 | AFF3 | 138 | Interchromosomal |
| MO_1051 | TBCK | PPA2 | 81 | Intrachromosomal |
| MO_1051 | CMAS | PIK3C2G | 73 | Intrachromosomal |
| MO_1051 | GPATCH8 | MPP2 | 24 | Intrachromosomal |
| MO_1051 | IKBKG | PLXNB3 | 3 | Intrachromosomal |
| MO_1051 | ITFG1 | NETO2 | 53 | Read through |
| MO_1051 | TXNDC11 | AK126539 | 2 | Read through |

TABLE 8

| SAMPLE | GENE | LOC([hg18) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1051 | B4GALT3 | chr1:159410453 | C | T | 32 | 145 | 0.22 | G167E | −2 | 125.1 |
| MO_1051 | GANAB | chr11:62154735 | C | T | 38 | 144 | 0.26 | D434N | 1 | 106.4 |
| MO_1051 | EFHD1 | chr2:233206867 | C | T | 13 | 27 | 0.48 | A70V | 0 | 106.2 |
| MO_1051 | NTN4 | chr12:94655867 | C | T | 24 | 96 | 0.25 | V258I | 3 | 94.6 |
| MO_1051 | SF1 | chr11:64291716 | G | C | 16 | 61 | 0.26 | H415Q | 0 | 84.1 |
| MO_1051 | QARS | chr3:49113864 | G | C | 19 | 82 | 0.23 | F268L | 0 | 68.8 |
| MO_1051 | ZNF296 | chr19:50267617 | C | T | 17 | 87 | 0.20 | W170* | −4 | 59.6 |
| MO_1051 | ZNF296 | chr19:50267290 | C | G | 26 | 100 | 0.26 | K279N | 0 | 59.6 |
| MO_1051 | PLXNB1 | chr3:48431630 | C | T | 28 | 98 | 0.29 | E1309K | 1 | 55.9 |
| MO_1051 | HDAC7 | chr12:46475778 | G | A | 18 | 51 | 0.35 | R277W | −3 | 50.0 |
| MO_1051 | TMEM214 | chr2:27116434 | C | T | 15 | 69 | 0.22 | S552F | −2 | 48.9 |

TABLE 8-continued

| SAMPLE | GENE | LOC([hg18]) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1051 | DAG1 | chr3:49545538 | C | A | 17 | 57 | 0.30 | Q864K | 1 | 44.0 |
| MO_1051 | DAG1 | chr3:49545403 | C | G | 17 | 76 | 0.22 | L819V | 1 | 44.0 |
| MO_1051 | DAG1 | chr3:49545024 | C | G | 30 | 124 | 0.24 | F692L | 0 | 44.0 |
| MO_1051 | DAG1 | chr3:49545321 | C | A | 34 | 100 | 0.34 | F791L | 0 | 44.0 |
| MO_1051 | PLEKHA6 | chr1:202486311 | C | T | 11 | 66 | 0.17 | E527K | 1 | 40.9 |
| MO_1051 | ZFP36L2 | chr2:43306032 | G | A | 34 | 127 | 0.27 | Q139* | −4 | 37.5 |
| MO_1051 | COMTD1 | chr10:76665477 | C | T | 37 | 109 | 0.4 | R42Q | 1 | 35.1 |
| MO_1051 | NACC1 | chr19:13107913 | C | T | 24 | 80 | 0.30 | R298W | −3 | 34.9 |
| MO_1051 | TOP1 | chr20:39160281 | G | A | 15 | 73 | 0.21 | E289K | 1 | 34.8 |
| MO_1051 | TOP1 | chr20:39160379 | G | C | 14 | 93 | 0.15 | K321N | 0 | 34.8 |
| MO_1051 | MGRN1 | chr16:4615042 | C | A | 20 | 71 | 0.28 | P27Q | −1 | 34.1 |
| MO_1051 | TUBA1B | chr12:47809566 | C | G | 15 | 69 | 0.22 | L70F | 0 | 34.1 |
| MO_1051 | THBS2 | chr6:169390445 | G | A | 32 | 97 | 0.33 | H201Y | 2 | 33.4 |
| MO_1051 | RAVER1 | chr19:10290021 | C | T | 7 | 37 | 0.19 | E642K | 1 | 31.7 |
| MO_1051 | LUC7L2 | chr7:138733981 | G | C | 11 | 48 | 0.23 | D85H | −1 | 30.5 |
| MO_1051 | PSMD1 | chr2:231645346 | G | A | 12 | 62 | 0.19 | G285D | −1 | 29.8 |
| MO_1051 | DHX30 | chr3:47862272 | G | A | 25 | 101 | 0.25 | E340K | 1 | 26.4 |
| MO_1051 | DYNC1H1 | chr14:101536124 | G | A | 10 | 34 | 0.29 | E1284K | 1 | 25.9 |
| MO_1051 | ZFAND6 | chr15:78201199 | C | T | 21 | 71 | 0.30 | S82F | −2 | 25.9 |
| MO_1051 | ZNF213 | chr16:3131032 | C | T | 28 | 114 | 0.25 | R355C | −3 | 25.5 |
| MO_1051 | TRIM26 | chr6:30262081 | C | G | 43 | 158 | 0.27 | E391Q | 2 | 25.4 |
| MO_1051 | SLC35B1 | chr17:45135284 | G | T | 19 | 61 | 0.31 | S284Y | −2 | 24.4 |
| MO_1051 | PIN1 | chr19:9810216 | G | A | 6 | 29 | 0.21 | V55I | 3 | 23.8 |
| MO_1051 | SLC38A10 | chr17:76840980 | C | G | 26 | 115 | 0.23 | E519Q | 2 | 23.8 |
| MO_1051 | ANKRD30A | chr10:37548514 | G | A | 11 | 53 | 0.21 | E124K | 1 | 23.3 |
| MO_1051 | USP22 | chr17:20856759 | G | A | 15 | 56 | 0.27 | S307L | −2 | 23.2 |
| MO_1051 | SLC15A3 | chr11:60466117 | G | C | 21 | 87 | 0.24 | S358C | −1 | 22.3 |
| MO_1051 | LRPPRC | chr2:44024438 | C | G | 45 | 154 | 0.29 | R779T | −1 | 20.5 |
| MO_1051 | SKI | chr1:2225661 | C | G | 29 | 102 | 0.28 | S515C | −1 | 20.4 |
| MO_1051 | CC2D1A | chr19:13899076 | G | C | 32 | 86 | 0.37 | E772Q | 2 | 20.1 |
| MO_1051 | RAP1GAP | chr1:21801938 | G | C | 27 | 104 | 0.26 | S495C | −1 | 18.9 |
| MO_1051 | HTATSF1 | chrX:135421575 | G | C | 17 | 94 | 0.18 | D669H | −1 | 18.7 |
| MO_1051 | TRIM41 | chr5:180593353 | C | G | 33 | 126 | 0.26 | F425L | 0 | 18.7 |
| MO_1051 | GATAD2B | chr1:152067127 | C | G | 36 | 152 | 0.24 | M107I | 1 | 18.7 |
| MO_1051 | LSS | chr21:46435568 | C | A | 27 | 79 | 0.34 | A693S | 1 | 18.5 |
| MO_1051 | LFNG | chr7:2533058 | C | G | 11 | 50 | 0.22 | F350L | 0 | 18.2 |
| MO_1051 | ABCG1 | chr21:42570107 | G | A | 26 | 115 | 0.23 | E191K | 1 | 16.9 |
| MO_1051 | TP53 | chr17:7518978 | C | T | 28 | 81 | 0.35 | G199E | −2 | 14.9 |
| MO_1051 | SHROOM3 | chr4:77879341 | C | T | 39 | 132 | 0.30 | Q330* | −4 | 14.9 |
| MO_1051 | HOXB7 | chr17:44040370 | T | C | 19 | 116 | 0.16 | T163A | 0 | 13.8 |
| MO_1051 | IMPAD1 | chr8:58041381 | G | A | 21 | 93 | 0.23 | S244F | −2 | 13.8 |
| MO_1051 | MAN2A1 | chr5:109218851 | G | A | 32 | 108 | 0.30 | E1030K | 1 | 13.3 |
| MO_1051 | SEC63 | chr6:108321444 | T | C | 7 | 49 | 0.14 | T537A | 0 | 13.0 |
| MO_1051 | KIAA0562 | chr1:3751724 | C | T | 16 | 57 | 0.28 | E160K | 1 | 13.0 |
| MO_1051 | DYRK1A | chr21:37784455 | C | G | 27 | 119 | 0.23 | S258C | −1 | 12.7 |
| MO_1051 | FAM8A1 | chr6:17708899 | G | C | 28 | 79 | 0.35 | E94Q | 2 | 12.6 |
| MO_1051 | KLHL17 | chr1:886979 | G | A | 24 | 95 | 0.25 | E159K | 1 | 12.4 |
| MO_1051 | BAZ1A | chr14:34322801 | C | G | 9 | 46 | 0.20 | D639H | −1 | 12.0 |
| MO_1051 | ZNF747 | chr16:30453456 | G | C | 25 | 97 | 0.26 | L16V | 1 | 11.6 |
| MO_1051 | ZNF646 | chr16:30996797 | G | A | 42 | 148 | 0.28 | D551N | 1 | 11.4 |
| MO_1051 | GMNN | chr6:24893986 | G | A | 35 | 117 | 0.30 | D204N | 1 | 11.4 |
| MO_1051 | NUP205 | chr7:134965696 | G | T | 14 | 43 | 0.33 | S1666I | −2 | 11.3 |
| MO_1051 | MANBA | chr4:103776138 | C | G | 16 | 86 | 0.19 | E697Q | 2 | 10.9 |
| MO_1051 | DHX29 | chr5:54594505 | C | G | 11 | 58 | 0.19 | E1180Q | 2 | 10.8 |
| MO_1051 | TRAPPC4 | chr11:118396114 | C | T | 41 | 120 | 0.34 | S132L | −2 | 10.7 |
| MO_1051 | PTPRT | chr20:40818629 | G | A | 19 | 78 | 0.24 | S249L | −2 | 10.5 |
| MO_1051 | PLEKHG5 | chr1:6453505 | C | G | 15 | 42 | 0.36 | Q473H | 0 | 10.3 |
| MO_1051 | USP36 | chr17:74315271 | C | T | 28 | 120 | 0.23 | E484K | 1 | 9.5 |
| MO_1051 | C5orf51 | chr5:41940308 | G | A | 20 | 85 | 0.24 | E28K | 1 | 9.5 |
| MO_1051 | NUFIP2 | chr17:24637332 | C | G | 33 | 122 | 0.27 | Q602H | 0 | 9.0 |
| MO_1051 | NUFIP2 | chr17:24638225 | C | A | 33 | 112 | 0.29 | D305Y | −3 | 9.0 |
| MO_1051 | NUFIP2 | chr17:24638363 | C | G | 33 | 119 | 0.28 | E259Q | 2 | 9.0 |
| MO_1051 | NUFIP2 | chr17:24637377 | C | G | 27 | 114 | 0.24 | E587D | 2 | 9.0 |
| MO_1051 | NUFIP2 | chr17:24637206 | C | G | 35 | 119 | 0.29 | Q644H | 0 | 9.0 |
| MO_1051 | NUFIP2 | chr17:24638147 | C | G | 35 | 113 | 0.31 | E331Q | 2 | 9.0 |
| MO_1051 | AFF4 | chr5:132260052 | C | G | 32 | 131 | 0.24 | L723F | 0 | 8.9 |
| MO_1051 | SIN3A | chr15:73451408 | G | A | 42 | 127 | 0.33 | R1263C | −3 | 8.9 |
| MO_1051 | C3orf63 | chr3:56650564 | G | C | 27 | 93 | 0.29 | D428E | 2 | 8.4 |
| MO_1051 | GBP2 | chr1:89355953 | G | C | 16 | 67 | 0.24 | P174A | −1 | 8.4 |
| MO_1051 | USP48 | chr1:21902699 | C | G | 10 | 37 | 0.27 | Splice acceptor | | 8.2 |
| MO_1051 | USP48 | chr1:21900628 | C | T | 8 | 38 | 0.21 | D893N | 1 | 8.2 |
| MO_1051 | USP48 | chr1:21902642 | C | T | 29 | 83 | 0.35 | E858K | 1 | 8.2 |
| MO_1051 | MCM2 | chr3:128807680 | G | A | 34 | 110 | 0.31 | E235K | 1 | 8.0 |
| MO_1051 | PTK2B | chr8:27350634 | G | A | 24 | 76 | 0.32 | E474K | 1 | 7.8 |
| MO_1051 | GPATCH8 | chr17:39832348 | C | T | 56 | 142 | 0.39 | D875N | 1 | 7.6 |

TABLE 8-continued

| SAMPLE | GENE | LOC([hg18]) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1051 | NT5DC1 | chr6:116528847 | C | G | 13 | 40 | 0.33 | L21V | 1 | 7.6 |
| MO_1051 | PANX1 | chr11:93502171 | C | G | 24 | 77 | 0.31 | F15L | 0 | 7.4 |
| MO_1051 | NOL8 | chr9:94116453 | C | T | 35 | 111 | 0.32 | E759K | 1 | 6.7 |
| MO_1051 | SRR | chr17:2171641 | G | T | 10 | 40 | 0.25 | G192V | −3 | 6.6 |
| MO_1051 | IGF1R | chr15:97273886 | G | C | 11 | 70 | 0.16 | K560N | 0 | 6.2 |
| MO_1051 | C12orf35 | chr12:32029593 | G | A | 24 | 100 | 0.24 | M1479I | 1 | 5.8 |
| MO_1051 | TRMT12 | chr8:125533520 | G | A | 36 | 127 | 0.28 | E391K | 1 | 5.6 |
| MO_1051 | ZNF770 | chr15:33062510 | C | T | 51 | 139 | 0.37 | A140T | 0 | 5.6 |
| MO_1051 | HSPA13 | chr21:14668314 | G | C | 34 | 129 | 0.26 | S304C | −1 | 5.5 |
| MO_1051 | GTF2E1 | chr3:121982852 | G | A | 49 | 150 | 0.33 | E389K | 1 | 4.8 |
| MO_1051 | ITSN1 | chr21:34091656 | G | A | 10 | 50 | 0.20 | E686K | 1 | 4.7 |
| MO_1051 | PGLYRP2 | chr19:15443755 | C | T | 28 | 99 | 0.28 | R430H | 0 | 4.7 |
| MO_1051 | ZKSCAN1 | chr7:99469022 | G | C | 10 | 35 | 0.29 | E320Q | 2 | 4.4 |
| MO_1051 | C2orf69 | chr2:200484591 | G | A | 32 | 100 | 0.32 | G62E | −2 | 4.4 |
| MO_1051 | MASP1 | chr3:188463101 | G | C | 20 | 59 | 0.34 | F113L | 0 | 4.4 |
| MO_1051 | RANBP6 | chr9:6003154 | C | G | 31 | 118 | 0.26 | L818F | 0 | 4.3 |
| MO_1051 | CD52 | chr1:26519322 | G | A | 43 | 131 | 0.33 | G43E | −2 | 4.2 |
| MO_1051 | CD97 | chr19:14378256 | C | G | 32 | 119 | 0.27 | F645L | 0 | 4.2 |
| MO_1051 | NFATC1 | chr18:75388521 | G | A | 11 | 79 | 0.14 | E917K | 1 | 4.1 |
| MO_1051 | PPP1R12B | chr1:200678203 | C | T | 13 | 85 | 0.15 | S516L | −2 | 3.8 |
| MO_1051 | PPTC7 | chr12:109474148 | C | T | 17 | 101 | 0.17 | D78N | 1 | 3.8 |
| MO_1051 | MYST3 | chr8:41953913 | G | A | 37 | 96 | 0.39 | S378L | −2 | 3.8 |
| MO_1051 | FLT4 | chr5:179980613 | C | G | 20 | 77 | 0.26 | G723A | 0 | 3.8 |
| MO_1051 | XDH | chr2:31426198 | G | A | 27 | 88 | 0.31 | R943W | −3 | 3.7 |
| MO_1051 | FYN | chr6:112089807 | C | T | 24 | 113 | 0.21 | R481Q | 1 | 3.6 |
| MO_1051 | HIVEP1 | chr6:12233605 | C | T | 40 | 148 | 0.27 | S1864F | −2 | 3.5 |
| MO_1051 | CYP4F2 | chr19:15858055 | C | G | 8 | 46 | 0.17 | E328Q | 2 | 3.5 |
| MO_1051 | TTC30A | chr2:178190124 | C | T | 14 | 53 | 0.26 | E518K | 1 | 3.4 |
| MO_1051 | CCDC99 | chr5:168953832 | G | A | 33 | 124 | 0.27 | E213K | 1 | 3.3 |
| MO_1051 | PIK3CA | chr3:180434779 | A | G | 27 | 88 | 0.31 | H1047R | 0 | 3.2 |
| MO_1051 | TBC1D7 | chr6:13413319 | G | A | 18 | 73 | 0.25 | S292L | −2 | 3.1 |
| MO_1051 | VSP13C | chr15:59948176 | C | T | 19 | 88 | 0.22 | E3613K | 1 | 3.0 |
| MO_1051 | EPDR1 | chr7:37956359 | G | C | 21 | 69 | 0.30 | D291H | −1 | 2.9 |
| MO_1051 | TACC1 | chr8:38764331 | G | A | 21 | 54 | 0.39 | G25E | −2 | 2.7 |
| MO_1051 | FGD6 | chr12:93999456 | C | G | 17 | 78 | 0.22 | E1422Q | 2 | 2.7 |
| MO_1051 | C14orf126 | chr14:30987094 | C | T | 22 | 88 | 0.25 | E167K | 1 | 2.6 |
| MO_1051 | CD22 | chr19:40523821 | G | A | 14 | 81 | 0.17 | A483T | 0 | 2.5 |
| MO_1051 | FAM83D | chr20:36988696 | G | A | 29 | 113 | 0.26 | D93N | 1 | 2.5 |
| MO_1051 | FAM83D | chr20:36988515 | G | A | 37 | 138 | 0.27 | E36K | 1 | 2.5 |
| MO_1051 | INTS2 | chr17:5739654 | C | G | 35 | 122 | 0.29 | E368Q | 2 | 2.5 |
| MO_1051 | C3orf15 | chr3:120910127 | G | C | 21 | 84 | 0.25 | Splice acceptor | | 2.5 |
| MO_1051 | AVIL | chr12:56489676 | C | G | 47 | 131 | 0.36 | E304Q | 2 | 2.5 |
| MO_1051 | MAP1B | chr5:71526970 | G | C | 7 | 39 | 0.18 | E678Q | 2 | 2.2 |
| MO_1051 | FJX1 | chr11:35597631 | G | C | 34 | 135 | 0.25 | D291H | −1 | 2.2 |
| MO_1051 | AR | chrX:66681775 | G | C | 30 | 77 | 0.39 | G21A | 0 | 2.1 |
| MO_1051 | ZNF446 | chr19:45212726 | C | G | 28 | 101 | 0.28 | S570* | −4 | 2.1 |
| MO_1051 | KIAA1549 | chr7:138254176 | G | C | 43 | 120 | 0.36 | P196A | −1 | 2.0 |
| MO_1051 | LYST | chr1:233987317 | G | C | 21 | 115 | 0.18 | L2316V | 1 | 2.0 |
| MO_1051 | ELOVL2 | chr6:11097983 | A | T | 27 | 113 | 0.24 | L235H | −3 | 2.0 |
| MO_1051 | C2orf67 | chr2:210648720 | G | A | 11 | 83 | 0.13 | S519L | −2 | 1.9 |
| MO_1051 | SEMA5B | chr3:124114940 | C | G | 39 | 139 | 0.28 | E768Q | 2 | 1.7 |
| MO_1051 | GRIN2D | chr19:53637221 | G | T | 15 | 74 | 0.20 | E815* | −4 | 1.6 |
| MO_1051 | PCNXL2 | chr1:231227606 | A | G | 15 | 127 | 0.12 | I1505T | −1 | 1.3 |
| MO_1051 | RABGAP1L | chr1:172455004 | C | T | 9 | 79 | 0.11 | P29L | −3 | 1.3 |
| MO_1051 | P2RX7 | chr12:120106623 | G | A | 37 | 103 | 0.36 | V475I | 3 | 1.1 |
| MO_1051 | MYBL1 | chr8:67641733 | C | T | 18 | 64 | 0.28 | E593K | 1 | 1.0 |
| MO_1051 | KIAA1524 | chr3:109755239 | C | T | 20 | 87 | 0.23 | E785K | 1 | 0.9 |
| MO_1051 | FEZ1 | chr11:124835703 | C | G | 18 | 51 | 0.35 | E190Q | 2 | 0.9 |
| MO_1051 | KIF21B | chr1:199215290 | G | A | 18 | 94 | 0.19 | L1373F | 0 | 0.8 |
| MO_1051 | LINGO4 | chr1:150040235 | G | A | 35 | 145 | 0.24 | P524S | −1 | 0.7 |
| MO_1051 | ST8SIA4 | chr5:100250047 | C | T | 42 | 138 | 0.30 | M134I | 1 | 0.6 |
| MO_1051 | FAM124B | chr2:224952709 | G | C | 11 | 82 | 0.13 | S398C | −1 | 0.6 |
| MO_1051 | ATOH8 | chr2:85835449 | C | T | 38 | 121 | 0.31 | S209L | −2 | 0.6 |
| MO_1051 | PNMA3 | chrX:151976633 | G | A | 28 | 134 | 0.21 | E189K | 1 | 0.5 |
| MO_1051 | BRIP1 | chr17:57115738 | C | T | 43 | 142 | 0.30 | E1151K | 1 | 0.5 |
| MO_1051 | MAML2 | chr11:95465186 | G | A | 39 | 128 | 0.30 | Q553* | −4 | 0.4 |
| MO_1051 | PLXNA4 | chr7:131562861 | C | T | 22 | 62 | 0.35 | V591I | 3 | 0.4 |
| MO_1051 | PHOSPHO1 | chr17:44657062 | C | G | 11 | 70 | 0.16 | E117Q | 2 | 0.4 |
| MO_1051 | MADCAM1 | chr19:452701 | G | A | 6 | 15 | 0.40 | D234N | 1 | 0.3 |
| MO_1051 | ABCA10 | chr17:64700956 | C | T | 29 | 94 | 0.31 | G557E | −2 | 0.3 |
| MO_1051 | ANKLE1 | chr19:17255720 | T | G | 54 | 155 | 0.35 | F383V | −1 | 0.3 |
| MO_1051 | FAT4 | chr4:126459294 | C | T | 31 | 129 | 0.24 | Q760* | −4 | 0.2 |
| MO_1051 | FHOD3 | chr18:32552148 | G | C | 14 | 68 | 0.21 | K788N | 0 | 0.2 |
| MO_1051 | KIRREL2 | chr19:41049157 | C | G | 30 | 127 | 0.24 | L684V | 1 | 0.2 |
| MO_1051 | FCAMR | chr1:205207606 | C | T | 41 | 162 | 0.25 | R18K | 2 | 0.2 |

TABLE 8-continued

| SAMPLE | GENE | LOC([hg18]) | REFERENCE | VARIANT | VAR FRAGS TUMOR | TUMOR TOTAL FRAGS | VAR FRAC TUMOR | PROTEIN | BLOSUM SCORE | EXPRESSION LEVEL (RPKM) |
|---|---|---|---|---|---|---|---|---|---|---|
| MO_1051 | CDH7 | chr18:61642928 | G | A | 15 | 61 | 0.25 | D288N | 1 | 0.2 |
| MO_1051 | DNAH7 | chr2:196560129 | C | T | 7 | 37 | 0.19 | E554K | 1 | 0.2 |
| MO_1051 | ADCY10 | chr1:166137634 | C | T | 43 | 176 | 0.24 | R109Q | 1 | 0.2 |
| MO_1051 | CCDC36 | chr3:49268748 | C | T | 42 | 134 | 0.31 | Q252* | −4 | 0.1 |
| MO_1051 | FBXO15 | chr18:69941604 | G | A | 11 | 34 | 0.32 | R297C | −3 | 0.1 |
| MO_1051 | HOXA2 | chr7:27107247 | G | A | 23 | 118 | 0.19 | Q252* | −4 | 0.1 |
| MO_1051 | PAPPA2 | chr1:175005504 | C | T | 23 | 72 | 0.32 | R1488C | −3 | 0.1 |
| MO_1051 | PI16 | chr6:37034898 | G | A | 19 | 58 | 0.33 | Splice acceptor | | 0.1 |
| MO_1051 | SHANK1 | chr19:55909256 | G | A | 15 | 54 | 0.28 | S212L | −2 | 0.1 |
| MO_1051 | C9orf131 | chr9:35033137 | C | G | 28 | 137 | 0.20 | Q171E | 2 | 0.1 |
| MO_1051 | ZPLD1 | chr3:103678980 | C | T | 39 | 140 | 0.28 | S375F | −2 | 0.1 |
| MO_1051 | CUBN | chr10:16995929 | G | A | 11 | 61 | 0.18 | H2474Y | 2 | 0.1 |
| MO_1051 | C9orf153 | chr9:88032614 | C | G | 35 | 126 | 0.28 | R73T | −1 | 0.1 |
| MO_1051 | BNC1 | chr15:81723220 | C | G | 39 | 148 | 0.26 | G596A | 0 | 0.1 |
| MO_1051 | ODZ1 | chrX:123382210 | C | T | 32 | 120 | 0.27 | M1531I | 1 | 0.0 |
| MO_1051 | CNKSR2 | chrX:21459906 | G | A | 21 | 70 | 0.30 | G368E | −2 | 0.0 |
| MO_1051 | DNAH6 | chr2:84775044 | G | T | 16 | 92 | 0.17 | D2485Y | −3 | 0.0 |
| MO_1051 | FCRLA | chr1:159948581 | G | A | 28 | 136 | 0.21 | E262K | 1 | 0.0 |
| MO_1051 | GCK | chr7:44153904 | C | T | 14 | 60 | 0.23 | E246K | 1 | 0.0 |
| MO_1051 | TYRP1 | chr9:12699141 | G | A | 40 | 151 | 0.26 | E525K | 1 | 0.0 |
| MO_1051 | RHAG | chr6:49694882 | G | T | 8 | 28 | 0.29 | Q104K | 1 | 0.0 |
| MO_1051 | RPH3A | chr12:111818909 | G | C | 16 | 60 | 0.27 | D672H | −1 | 0.0 |
| MO_1051 | POU6F2 | chr7:39213708 | G | A | 34 | 102 | 0.33 | G159R | −2 | 0.0 |
| MO_1051 | MYT1L | chr2:1905497 | G | A | 54 | 169 | 0.32 | P351S | −1 | 0.0 |
| MO_1051 | LRRTM4 | chr2:77600343 | C | A | 57 | 180 | 0.32 | D54Y | −3 | 0.0 |
| MO_1051 | ALK | chr2:29310018 | C | T | 32 | 109 | 0.29 | E802K | 1 | 0.0 |
| MO_1051 | CIB4 | chr2:26717641 | C | G | 25 | 93 | 0.27 | E16Q | 2 | 0.0 |
| MO_1051 | A2ML1 | chr12:8912114 | C | T | 40 | 91 | 0.44 | L1319F | 0 | 0.0 |
| MO_1051 | GABRR1 | chr6:89945354 | C | T | 42 | 127 | 0.33 | E426K | 1 | 0.0 |
| MO_1051 | POU6F2 | chr7:39213709 | G | A | 35 | 106 | 0.33 | G159E | −2 | 0.0 |
| MO_1051 | NKX2-3 | chr10:101285073 | G | C | 11 | 44 | 0.25 | D234H | −1 | 0.0 |
| MO_1051 | ATP12A | chr13:24181895 | C | G | 15 | 83 | 0.18 | L898V | 1 | 0.0 |
| MO_1051 | CBLN4 | chr20:54009229 | G | A | 11 | 66 | 0.17 | H125Y | 2 | 0.0 |
| MO_1051 | SLC1A6 | chr19:14944567 | G | C | 28 | 101 | 0.28 | F52L | 0 | 0.0 |
| MO_1051 | FOXI2 | chr10:129425568 | C | T | 13 | 27 | 0.48 | P14L | −3 | 0.0 |
| MO_1051 | OR5K3 | chr3:99592974 | C | T | 17 | 64 | 0.27 | R259* | −4 | 0.0 |
| MO_1051 | SPINT4 | chr20:43786011 | G | T | 18 | 84 | 0.21 | R65I | −3 | 0.0 |
| MO_1051 | SI | chr3:166209775 | C | G | 13 | 80 | 0.16 | D1389H | −1 | 0.0 |
| MO_1051 | TMEM202 | chr15:70487239 | C | G | 6 | 37 | 0.16 | S258C | −1 | 0.0 |
| MO_1051 | HELQ | chr4:84569908 | C | G | 10 | 47 | 0.21 | D771H | −1 | NA |
| MO_1051 | AKR1E2 | chr10:4867919 | C | A | 20 | 62 | 0.32 | S126* | −4 | NA |
| MO_1051 | EPG5 | chr18:41714088 | C | T | 12 | 33 | 0.36 | E1873K | 1 | NA |
| MO_1051 | BRAT1 | chr7:2549466 | G | A | 10 | 42 | 0.24 | S274F | −2 | NA |

TABLE 9

| Sample | Segment (hg18) | Genes in this region | Span (bp) | Number of exons | Copy number ratio (gains) |
|---|---|---|---|---|---|
| MO_1051 | chr12:44407518-44410034 | LOC400027, ARID2 | 2,516 | 2 | 3.01 |
| MO_1051 | chr6:114285600-114288048 | MARCKS | 2448 | 2 | 2.94 |
| MO_1051 | chr1:150750710-151082749 | KPRP, C1orf68, Late envelope proteins | 332,039 | 19 | 2.34 |
| MO_1051 | chr11:6188000-6189418 | C11orf42, FAM160A2 | 1418 | 3 | 2.07 |
| MO_1051 | chr20:60909386-60938896 | OGFR, COL9A3 | 29,510 | 32 | 1.82 |
| MO_1051 | chrX:34058471-34871964 | TMEM47 | 813,493 | 10 | 1.66 |
| MO_1051 | chrX:107291498-107822692 | COL4A6, COL4A5 | 531,194 | 87 | 1.61 |
| MO_1051 | chr1:151123700-225910130 | ABL2, CAMK1G, CDC42BPA, CLK2, DDR2DYRK3, ELK4, FCGR2B, IKBKE, INSRRMAPKAPK2, MARK1, MDM4, MUC1, NEK2NEK7, NPR1, NTRK1, NUAK2, PBX1PRCC, PTGS2, RNASEL, RPS6KC1, SCYL3SDHC, SLC45A3, TPM3, TPR, UHMK1 | 74,786,430 | 6263 | 1.59 |

| Sample | Segment (hg18) | Genes in this region | Span (bp) | Number of exons | Copy number ratio (losses) |
|---|---|---|---|---|---|
| MO_1051 | chr8:935432-947796 | ERICH1-AS1 | 12,364 | 2 | 0.13 |
| MO_1051 | chr16:87826705-87827520 | ENSG00000205014 | 815 | 2 | 0.15 |
| MO_1051 | chr10:2787544-2920752 | — | 133,208 | 2 | 0.18 |

TABLE 9-continued

| | | | | | |
|---|---|---|---|---|---|
| MO_1051 | chr7:157748520-157812260 | PTPRN2 | | 63,740 | 5 | 0.21 |
| MO_1051 | chr12:48557874-48559872 | FAIM2 | | 1,998 | 3 | 0.22 |
| MO_1051 | chr12:131422038-131542490 | — | | 120,452 | 5 | 0.24 |
| MO_1051 | chr4:88754446-88756667 | DSPP | | 2,221 | 3 | 0.31 |
| MO_1051 | chr6:168856780-168857712 | — | | 932 | 3 | 0.31 |
| MO_1051 | chr9:95464514-95465753 | PHF2 | | 1,239 | 3 | 0.35 |
| MO_1051 | chr7:141566309-141567246 | — | | 937 | 3 | 0.36 |
| MO_1051 | chr9:138860132-138861212 | C9orf172 | | 1,080 | 4 | 0.41 |
| MO_1051 | chr17:11085763-11939730 | SHISA6, DNAH9, ZNF18, MAP2K4 | | 853,967 | 88 | 0.41 |

TABLE 10

| Sample | 5' Gene | 3' Gene | Number of Supporting Reads | Type |
|---|---|---|---|---|
| MO_1081 | SLC45A3 | FGFR2 | 2020 | Interchromosomal |
| MO_1081 | ST7 | CAV1 | 200 | Intrachromosomal |
| MO_1081 | MAP7 | PERP | 161 | Intrachromosomal |
| MO_1081 | LAS1L | OPHN1 | 33 | Intrachromosomal |
| MO_1081 | BRE | RBKS | 20 | Intrachromosomal |
| MO_1081 | BMPR1B | SMARCAD1 | 22 | Intrachromosomal |

TABLE 11

| Cancer type | Data source | Sample number | FGFR Fusion |
|---|---|---|---|
| BRCA (Breast cancer) | TCGA | 746 | 3 |
| LUSC (Lung squamous carcinoma) | TCGA | 222 | 6 |
| BLCA (Bladder Urothelial Carcinoma) | TCGA | 85 | 3 |
| GBM (Glioblastoma multiforme) | TCGA | 163 | 2 |
| HNSC (Head and neck squamous cell carcinoma ) | TCGA | 284 | 2 |
| THCA (Papillary thyroid cancer) | TCGA | 237 | 1 |
| LUAD (Lung adenocarcinoma) | TCGA | 299 | 0 |
| LIHC (Liver Hepatocellular Carcinoma) | TCGA | 17 | 0 |
| MI-ONCOSEQ patients | U Michigan | 90 | 4 |
| Research cohorts | U Michigan | 232 | 3 |
| Total: | | 2375 | 24 |

Research Cohorts from the University of Michigan

| Cancer type | Sample number | Cell line | Tissue |
|---|---|---|---|
| Bladder | 2 | 2 | 0 |
| Breast | 93 | 53 | 40 |
| Cervical | 9 | 9 | 0 |
| Colon | 9 | 9 | 0 |
| Leukemia | 4 | 0 | 4 |
| Lymphoma | 5 | 5 | 0 |
| Melanoma | 7 | 7 | 0 |
| Oral | 6 | 6 | 0 |
| Pancreas | 25 | 25 | 0 |
| Prostate | 31 | 0 | 31 |
| Rare cancer | 41 | 41 | 0 |
| Total: | 232 | 157 | 75 |

TABLE 12

| 5' Gene | 3' Gene | Sample ID | Cancer type | Fusion | Predominant isoform | Isoform ratio (major/minor) |
|---|---|---|---|---|---|---|
| FGFR2 fusions | | | | | | |
| FGFR2 | AFF3 | MO_1051 (MI-ONCOSEQ case) | Breast | Inter | IIIc | 6.7 |
| FGFR2 | CCDC6 | TCGA-D8-A13Z-01A-11R-A115-07 | Breast | Intra | IIIc | 72.9 |
| FGFR2 | CASP7 | TCGA-AN-A0AL-01A-11R-A00Z-07 | Breast | Intra | IIIc | 14.8 |
| FGFR2 | BICC1 | MO_1036 (MI-ONCOSEQ case) | Cholangiocarcinoma | Intra | IIIb | 13.5 |
| FGFR2 | BICC1 | MO_1039 (MI-ONCOSEQ case) | Cholangiocarcinoma | Intra | IIIb | 5.9 |
| FGFR2 | KIAA1967 | TCGA-66-2765-01A-01R-0851-07 | LUSC | Inter | IIIc | 24.3 |
| FGFR2 | OFD1 | TCGA-BJ-A0Z0-01A-11R-A10U-07 | THCA | Inter | IIIc | 67.2 |
| SLC45A3 | FGFR2 | MO_1081 (MI-ONCOSEQ case) | Prostate | Inter | IIIb | 1.8 |
| FGFR3 fusions | | | | | | |
| FGFR3 | BAIAP2L1 | SW780 (Internal collection: cell line) | Bladder | Inter | IIIb | 10.2 |
| FGFR3 | TACC3 | RT4 (Internal collection: cell line) | Bladder | Intra | IIIb | 7.9 |
| FGFR3 | TACC3 | C9 (Internal collection: cell line) | Oral cancer | Intra | IIIb | 12.7 |
| FGFR3 | TACC3 | TCGA-CF-A3MF-01A-12R-A21D-07 | Bladder | Intra | IIIc | 1.9 |
| FGFR3 | TACC3 | TCGA-CF-A3MG-01A-11R-A20F-07 | Bladder | Intra | IIIb | 40.6 |
| FGFR3 | TACC3 | TCGA-CF-A3MH-01A-11R-A20F-07 | Bladder | Intra | IIIb | 12.3 |
| FGFR3 | TACC3 | TCGA-27-1835-01A-01R-1850-01 | GBM | Intra | IIIc | 8.4 |
| FGFR3 | TACC3 | TCGA-76-4925-01A-01R-1850-01 | GBM | Intra | IIIc | 28.9 |
| FGFR3 | TACC3 | TCGA-CR-6473-01A-11R-1873-07 | HNSC | Intra | IIIb | 11.1 |
| FGFR3 | TACC3 | TCGA-CV-7100-01A-11R-2016-07 | HNSC | Intra | IIIb | 14.5 |
| FGFR3 | TACC3 | TCGA-66-2786-01A-01R-0851-07 | LUSC | Intra | IIIb | 34.4 |
| FGFR3 | TACC3 | TCGA-39-5024-01A-21R-1820-07 | LUSC | Intra | IIIb | 10.1 |
| FGFR3 | TACC3 | TCGA-22-4607-01A-01R-1201-07 | LUSC | Intra | IIIb | 9.5 |
| FGFR3 | TACC3 | TCGA-34-2608-01A-02R-0851-07 | LUSC | Intra | IIIb | 20.8 |
| FGFR1 fusions | | | | | | |
| ERLIN2 | FGFR1 | TCGA-D8-A1JC-01A-11R-A13Q-07 | Breast | Intra | IIIc | 14.5 |
| BAG4 | FGFR1 | TCGA-22-5480-01A-01R-1635-07 | LUSC | Intra | IIIc | 20.9 |

TABLE 13

| GENE/ISOFORM | TRANSCRIPT | PROTEIN |
|---|---|---|
| FGFR1 IIIc | NM_023110 | NP_075598 |
| FGFR2 IIIb | NM_022970 | NP_075259 |
| FGFR2 IIIc | NM_000141 | NP_000132 |
| FGFR3 IIIb | NM_001163213 | NP_001156685 |
| FGFR3 IIIc | NM_000142 | NP_000133 |
| AFF3 | NM_002285 | NP_002276 |
| BAG4 | NM_004874 | NP_004865 |
| BAIAP2L1 | NM_018842 | NP_061330 |
| BICC1 | NM_001080512 | NP_001073981 |

TABLE 13-continued

| GENE/ISOFORM | TRANSCRIPT | PROTEIN |
|---|---|---|
| CASP7 | NM_001227 | NP_001218 |
| CCDC6 | NM_005436 | NP_005427 |
| ERLIN2 | NM_007175 | NP_009106 |
| KIAA1967 | NM_021174 | NP_066997 |
| OFD1 | NM_003611 | NP_003602 |
| SLC45A3 | NM_033102 | NP_149093 |
| TACC3 | NM_006342 | NP_006333 |

TABLE 14

| 5' Gene | Junction Sequence | 3' Gene | SEQ ID NO |
|---|---|---|---|
| BAG4 exon 2 | AGACCAGAATTGCAAGGCCAG\|GTCCGTTATGCCACCTGGAGC | FGFR1 exon 9 | 1 |
| ERLIN2 exon 10 | CCGCAGAAACTACGAGTTGAT\|GGTCAGTTTGAAAAGGAGGAT | FGFR1 exon 4 | 2 |
| FGFR2 exon 19 | CTCACTCTCACAACCAATGAG\|GAGAGTAGATCTGGAGAAACC | AFF3 exon 8 | 3 |
| FGFR2 exon 19 | CTCACTCTCACAACCAATGAG\|ATCATGGAGGAAACAAATACG | BICC1 exon 3 | 4 |
| FGFR2 exon 19 | CTCACTCTCACAACCAATGAG\|ATGGCAGATGATCAGGGCTGT | CASP7 exon 4 | 5 |
| FGFR2 exon 19 | CTCACTCTCACAACCAATGAG\|CAAGCCAGGGCTGAGCAGGAA | CCDC6 exon 2 | 6 |
| FGFR2 exon 19 | CTCACTCTCACAACCAATGAG\|GGTGGGGAGAAACAGCGGGTC | KIAA1967 exon 5 | 7 |
| FGFR2 exon 19 | CTCACTCTCACAACCAATGAG\|ACACAACTTCGAAACCAGCTA | OFD1 exon 3 | 8 |
| SLC45A3 exon 1 | ACAGCCGCGCGCCTCGGCCAG\|TGACTGCAGCAGCAGCGGCAG | FGFR2 exon 3b | 9 |
| FGFR3 exon 18 | CTTACCGTGACGTCCACCGAC\|AATGTTATGGAACAGTTCAAT | BAIAP2L1 exon 2 | 10 |
| FGFR3 exon 18 | CTTACCGTGACGTCCACCGAC\|GTGCCAGGCCCACCCCCAGGT | TACC3 exon 10 | 11 |
| FGFR3 exon 18 | CTTACCGTGACGTCCACCGAC\|GTAAAGGCGACACAGGAGGAG | TACC3 exon 11 | 12 |
| FGFR3 intron 18 | GCTGAGGTGTGGGCGGGCCT\|TCTGGCCCAGGTGCCCTGGCT | TACC3 exon 4 | 13 |

TABLE 15

| | | SEQ ID NO. |
|---|---|---|
| Cloning of FGFR fusion alleles | | |
| FGFR2 FL-S | CAACGGTCCGACCATGGTCAGCTGGGGTCGTTTCATC | 14 |
| CCDC6 TAG-AS | GAACGGACCGAAAGGCTGGGAGGAGGGGTG | 15 |
| BICC1 TAG-AS | GAACGGACCGCGGCCACTGACACTAGCAATGT | 16 |
| FGFR3 FL-S | CAACGGTCCGACCATGGGCGCCCCTGCCT | 17 |
| TACC3 TAG-AS | CAACGGACCGATCTTCTCCATCTTGGAGATGAG | 18 |
| BAIAP2L1 TAG-AS | GAACGGACCGCGAATGATGGGTGCCGAGCGAT | 19 |
| Cloning of FGFR fusion partners | | |
| BAIAP2L1 DIM-S | CAACGGTCCGACCATGAATGTTATGGAACAGTTCAATCC | 20 |
| BAIAP2L1 TAG-AS | GAACGGACCGCGAATGATGGGTGCCGAGCGAT | 21 |
| BICC1 DIM-S | GAACGGTCCGACCATGATCATGGAGGAAACAAATACGCAGA | 22 |
| BICC1 TAG-AS | CAACGGACCGCGGCCACTGACACTAGCAATGTCTGA | 23 |
| TACC3 DIM-S | CAACGGTCCGACCATGGTGCCAGGCCCACCCCCAGGTGTT | 24 |
| TACC3 TAG-AS | CAACGGACCGATCTTCTCCATCTTGGAGATGAG | 25 |
| KIAA1967CPO-S | GAACGGTCCGACCATGGGTGGGAGAAACAGCGGGTCTTCA | 26 |
| KIAA1967 TAG-AS | CTTCGGACCGTTGCTAGGTGCCGGCTCCTCCTT | 27 |
| CCDC6 DIM-S | GAACGGTCCGACCATGCAAGCCAGGGCTGAGCAGGAAGAA | 28 |
| CCDC6 TAG-AS | GAACGGACCGAAAGGCTGGGAGGAGGGGTG | 29 |
| CIT DIM-S | CAACGGTCCGACCATGGCACATAGAGATGAAATCCAGCGCAA | 30 |
| CIT TAG-AS | CAACGGACCGACTGAAGACTGGTCCCAGACCTT | 31 |
| Quantitative RT-PCR primers | | |
| FGFR2-AFF3 QPCR-F | CCAACTGCACCAACGAACTG | 32 |
| FGFR2-AFF3 QPCR-R | GTGGAAGCCAGGTCATCTCC | 33 |
| FGFR2-BICC QPCR-F | GCTGCTGAAGGAAGGACACA | 34 |
| FGFR2-BICC QPCR-R | ATGGCCAAGCAATCTGCGTA | 35 |
| FGFR3-BAIAP2L1 QPCR-F | GACCTGGACCGTGTCCTTAC | 36 |
| FGFR3-BAIAP2L1 QPCR-R | GATCTTGGCCACTCCATCGT | 37 |

Although a variety of embodiments have been described in connection with the present disclosure, it should be understood that the claimed invention should not be unduly limited to such specific embodiments. Indeed, various modifications and variations of the described compositions and methods of the invention will be apparent to those of ordinary skill in the art and are intended to be within the scope of the following claims.

We claim:

1. A method for detecting the presence of a gene fusion in a sample from a subject comprising
   (a) contacting a biological sample from a subject with at least a first gene fusion informative reagent for identification of a SLC45A3-FGFR2 gene fusion having SEQ ID NO: 9, wherein said at least a first gene fusion informative reagent is probe that specifically hybridizes to the SLC45A3-FGFR2 junction of SEQ ID NO: 9, and
   (b) detecting hybridization of the probe to the sample, and thus, detecting the presence of said gene fusion in said sample using said reagent.

2. A method for detecting the presence of a gene fusion in a sample from a subject comprising
   (a) contacting a biological sample from a subject with at least a first gene fusion informative reagent for identification of a SLC45A3-FGFR2 gene fusion having SEQ ID NO: 9, wherein said at least a first gene fusion informative reagent is a pair of amplification primers that amplify the SLC45A3-FGFR2 junction of SEQ ID NO: 9, and
   (b) amplifying a nucleic acid comprising the SLC45A3-FGFR2 junction, and detecting the amplification product comprising the junction of SEQ ID NO: 9, thus detecting the presence of said gene fusion in said sample using said reagent.

3. The method of claim 2, wherein said pair of amplification primers comprises a first primer that hybridizes to exon 1 of SLC45A3 and a second primer that hybridizes to exon 3b of FGFR2.

4. A method for detecting the presence of a gene fusion in a sample from a subject comprising
   (a) contacting a biological sample from a subject with at least a first gene fusion informative reagent for identification of a SLC45A3-FGFR2 gene fusion having SEQ ID NO: 9, wherein said at least a first gene fusion informative reagent is a sequencing primer that binds SEQ ID NO: 9

(b) generating an extension product that includes the fusion junction of SEQ ID NO: 9, and (c) detecting the extension product comprising the junction of SEQ ID NO: 9, thus detecting the presence of said gene fusion in said sample using said reagent.

5. The method of claim 1, 2 or 4, wherein the sample is selected from the group consisting of tissue, blood, plasma, serum, cells and tissues.

6. The method of claim 1, 2, or 4, wherein said reagent is labeled.

* * * * *